United States Patent [19]
Hoekema et al.

[11] Patent Number: 5,925,804
[45] Date of Patent: Jul. 20, 1999

[54] PRODUCTION OF TREHALOSE IN PLANTS

[75] Inventors: Andreas Hoekema, Oegstgeest; Jan Pen, Leiden; Mirjam Petronella Does, Amsterdam; Petrus Josephus Maria Van Den Elzen, Voorhout, all of Netherlands

[73] Assignee: Mogen International NV, Leiden, Netherlands

[21] Appl. No.: 08/569,150

[22] PCT Filed: Jun. 30, 1994

[86] PCT No.: PCT/EP94/02167

§ 371 Date: Dec. 21, 1995

§ 102(e) Date: Dec. 21, 1995

[87] PCT Pub. No.: WO95/01446

PCT Pub. Date: Jan. 12, 1995

[30] Foreign Application Priority Data

Jun. 30, 1993 [EP] European Pat. Off. .............. 93201904

[51] Int. Cl.⁶ ............... A01H 5/00; A01H 5/10; C12N 5/14; C12N 15/31; C12N 15/52; C12N 15/82

[52] U.S. Cl. ............ 800/295; 435/320.1; 435/419; 435/468; 536/23.2; 536/23.7; 800/284; 800/317; 800/317.2

[58] Field of Search ............... 435/320.1, 252.3, 435/172.3, 240.4, 97, 419, 69.1; 536/23.2, 23.7; 800/205, DIG. 40, DIG. 42

[56] References Cited

U.S. PATENT DOCUMENTS 5,422,254 6/1995 Londesborough et al. .............. 435/97

FOREIGN PATENT DOCUMENTS 0451896 10/1991 European Pat. Off. .
0577915 1/1994 European Pat. Off. .
9317093 9/1993 WIPO .

OTHER PUBLICATIONS

Quillet, M., et al. 'Sur l'accumulation . . . ' Comptes Rendues Acad. Sc. Paris, vol. 259, Jul. 20, 1964, pp. 635–637.

Adams, R.P., et al. 'Comparison of Free Sugars . . . ' Biological Abstracts, vol. 90, 1990, Philadelphia PA, US; abstract No. 80013.

Bell, W., et al. 'Characaterization of the 56–KDa . . . ' European Journal of Biochemistry, vol. 209, No. 3, Nov. 1992, pp. 951–959.

Gonzales, M.I., et al. 'Molecular Cloning of CIFI, . . . ' Yeast, vol. 8, 1992, pp. 183–192.

Kaasen, I. et al. 'Molecular Cloning and Physical . . . ' J. Bacteriology, vol. 174, No. 3, Feb. 1992, pp. 889–898.

EMBL Sequence Database Rel. Acc. No. X69160, May 27, 1993.

McDougall, J., et al. 'A Yeast Gene for . . . ' FEMS Microbiol. Lett., vol. 107, 1993. pp. 25–30.

Tomos, D. 'Life without Water' Current Biology, vol. 2, No. 11, 1992. pp. 594–596.

Countinho, C. et al. 'Trehalose as Cryoprotectant . . . ' J. Biotechnology, vol. 7, No. 1, 1988, pp. 23–32.

Comparison of Free Sugars in Growing and Desiccated Plants of *Selaginella lepidophylla*, Robert P. Adams, et al Biochemical Systematics and Ecology, vol. 18 No. 2/3 pp. 107–110 1990.

Tomos (1992) Current Biology 2(11): 594–596.

Coutinho, et al. (1988) Journal of Biotechnology 7: 23–32.

Kassen, et al. (Feb. 1992) Journal of Bacteriology 174 (3): 889–898.

McDougall, EMBL Sequence Database Rel. Acc. No. X69160, May 27, 1993.

*Primary Examiner*—Douglas W. Robinson
*Assistant Examiner*—Amy J. Nelson
*Attorney, Agent, or Firm*—Ladas & Parry

[57] ABSTRACT

A nucleic acid having (i) a DNA molecule which, when expressed in a plant or plant cell, increases the trehalose content of the plant or plant cell, the DNA molecule encoding an *E. coli* trehalose phosphate synthase, and (ii) a plant expressible promoter operatively coupled to the DNA molecule. Also, a method for obtaining a plant with increased trehalose production by introducing into a recipient cell of a plant, a plant expressible gene which, when expressed in a plant or plant cell increases the trehalose content of the plant or plant cell. The plant expressible gene is an *E. coli* trehalose phosphate synthase gene which is operably linked to: a) a transcriptional initiation region that is functional in the plant, and b) a DNA molecule encoding a selectable marker gene that is functional in the plant. The method includes a step of regenerating a plant from the recipient cell under conditions that allow for selection for the presence of the selectable marker gene.

30 Claims, 11 Drawing Sheets

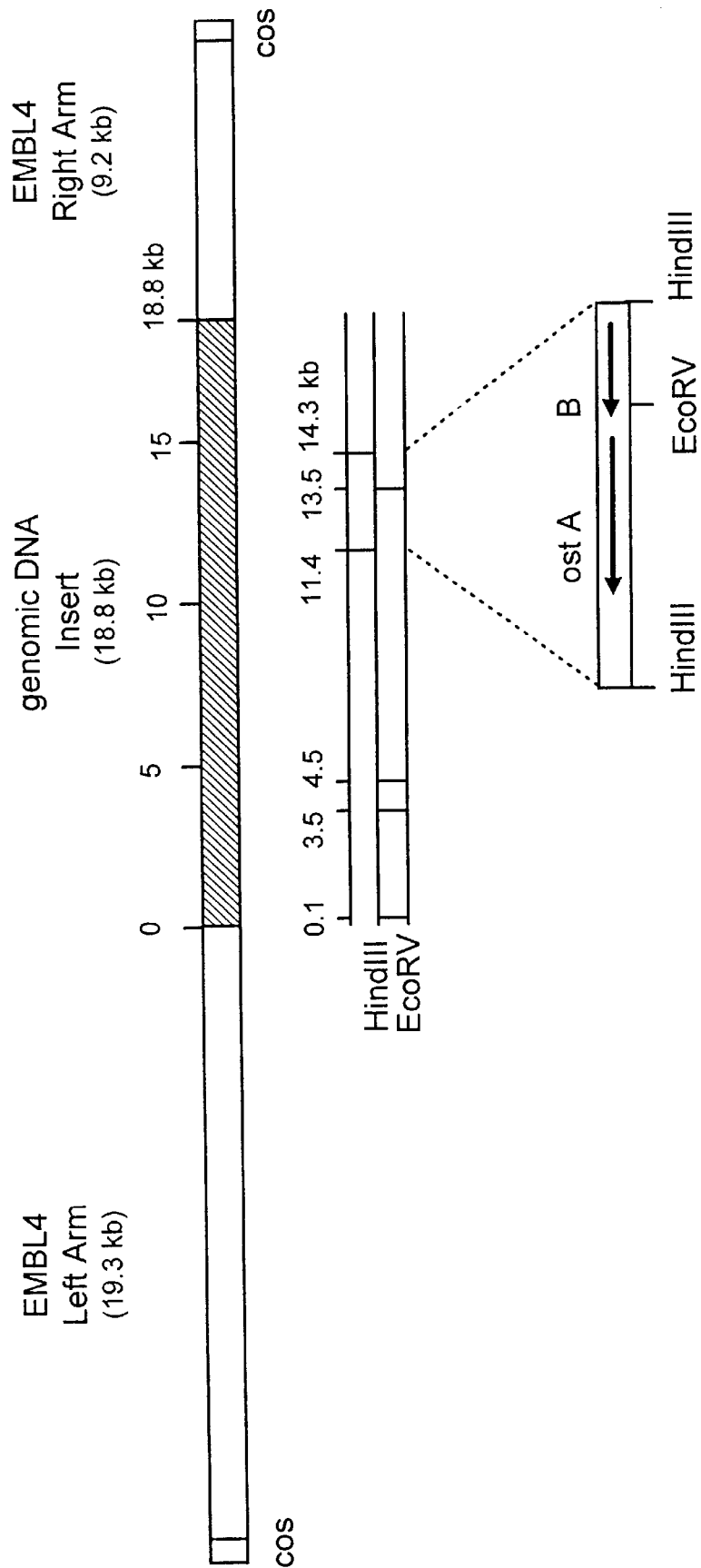
F I G. 2

```
      |        |        |        |        |        |        |
      1        10       20       30       40       50       60
  1   CTAGGTCGTG ATTCTGATAC AGGTGGCCAG GTGAAGTATG TAGTAGAGCT TGCTCGAGCA    60
 61   CTTGCAAACA TGAAAGGAGT TCACCGAGTT GATCTCTTGA CTCGGCAGAT CACATCCCCA   120
121   GAGGTTGATT CTAGCTATGG TGAGCCAATT GAGATGCTCT CATGCCCATC TGATGCTTTG   180
181   GCTGCTGTGG TGCCTACTAT TCGGATCCCT GCGGACCAGG TGACAAGATA TTCCAAAAGA   240
241   ATTTACATAC CAGAATTTGT TGATGGAGCA TTAAGCCACA TTGTGAATAT GGCAAGGGCT   300
301   ATAGGGGAGC AAGTCAATGC TGGAAAAGCA GTGTGGCCTT ACGTGATACA TGGGCACTAT   360
361   GCCGATGCTG                                                         370
      |        |        |        |        |        |        |
      1        10       20       30       40       50       60
```

FIG. 3

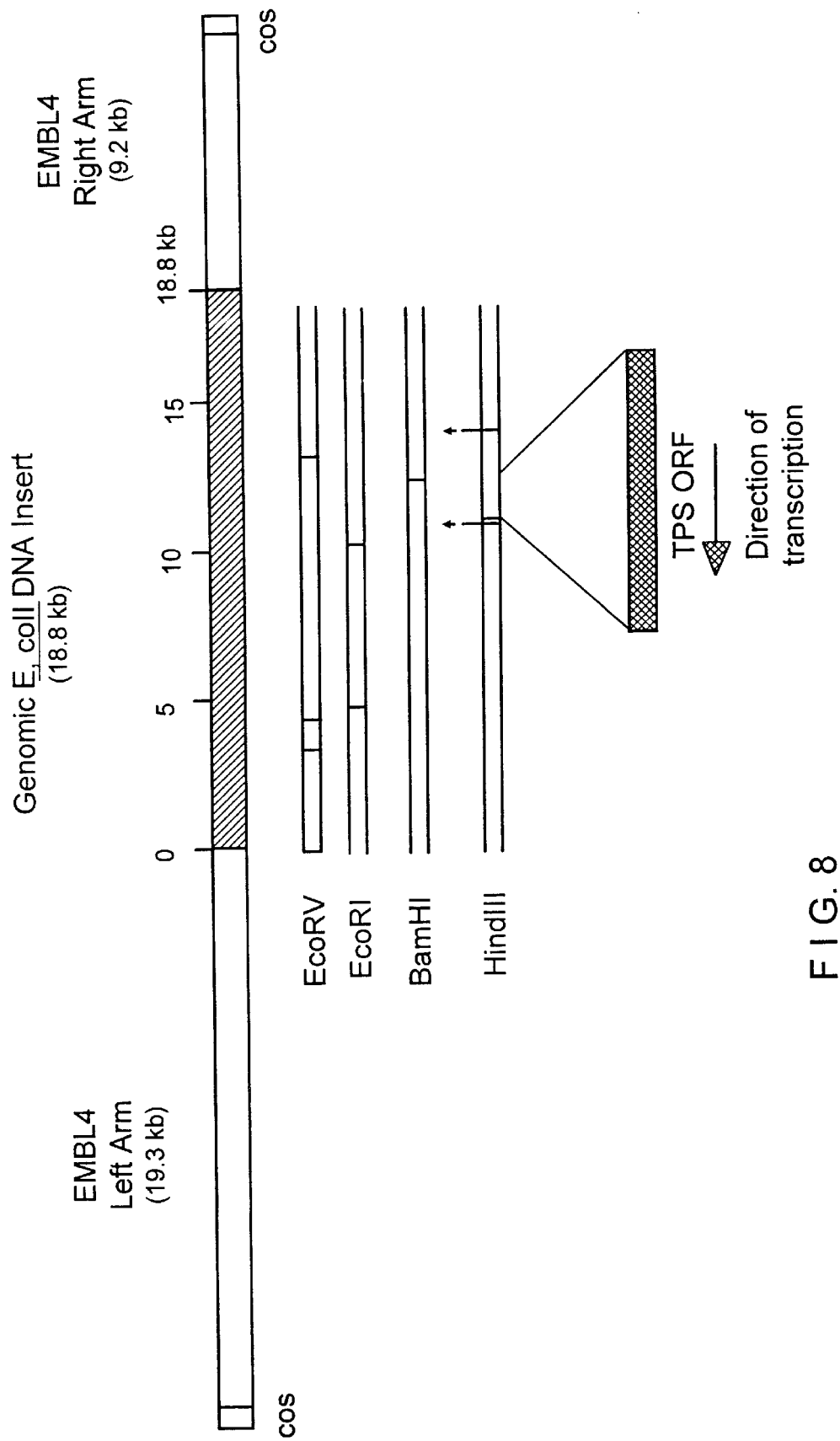
F I G. 8

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
       (A) LENGTH: 370 base pairs
       (B) TYPE: nucleic acid
       (C) STRANDEDNESS: double
       (D) TOPOLOGY: linear (ii) MOLECULE TYPE: cDNA to mRNA (iii) HYPOTHETICAL: NO (vi) ORIGINAL SOURCE:
       (A) ORGANISM: Solanum tuberosum
       (B) STRAIN: Desiree
       (F) TISSUE TYPE: Leaf (xi) SEQUENCE DESCRIPTION: SEQ ID NO: 1:

```
CTAGGTCGTG ATTCTGATAC AGGTGGCCAG GTGAAGTATG TAGTAGAGCT TGCTCGAGCA      60

CTTGCAAACA TGAAAGGAGT TCACCGAGTT GATCTCTTGA CTCGGCAGAT CACATCCCCA     120

GAGGTTGATT CTAGCTATGG TGAGCCAATT GAGATGCTCT CATGCCCATC TGATGCTTTG     180

GCTGCTGTGG TGCCTACTAT TCGGATCCCT GCGGACCAGG TGACAAGATA TTCCAAAGA      240

ATTTACATAC CAGAATTTGT TGATGGAGCA TTAAGCCACA TTGTGAATAT GGCAAGGGCT     300

ATAGGGAGC AAGTCAATGC TGGAAAAGCA GTGTGGCCTT ACGTGATACA TGGGCACTAT      360

GCCGATGCTG                                                            370
```

(2) INFORMATION FOR SEQ ID NO: 2:

(i) SEQUENCE CHARACTERISTICS:
       (A) LENGTH: 1446 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (vi) ORIGINAL SOURCE:
       (A) ORGANISM: Escherichia coli (vii) IMMEDIATE SOURCE:
       (B) CLONE: 7F11

(viii) POSITION IN GENOME:
       (B) MAP POSITION: 41-42'

(ix) FEATURE:
       (A) NAME/KEY: CDS
       (B) LOCATION: 19..1446
       (D) OTHER INFORMATION: /product= "trehalose phosphate
           synthase" /gene= "otsA"

(xi) SEQUENCE DESCRIPTION: SEQ ID NO: 2:

```
GAGAAAATAA CAGGAGTG ATG ACT ATG AGT CGT TTA GTC GTA GTA TCT AAC       51
                   Met Thr Met Ser Arg Leu Val Val Val Ser Asn
                    1               5                      10

CGG ATT GCA CCA CCA GAC GAG CAC GCC GCC AGT GCC GGT GGC CTT GCC       99
Arg Ile Ala Pro Pro Asp Glu His Ala Ala Ser Ala Gly Gly Leu Ala
            15                  20                  25

GTT GGC ATA CTG GGG GCA CTG AAA GCC GCA GGC GGA CTG TGG TTT GGC      147
```

-continued

```
                Val Gly Ile Leu Gly Ala Leu Lys Ala Ala Gly Gly Leu Trp Phe Gly
                         30                  35                  40

TGG AGT GGT GAA ACA GGG AAT GAG GAT CAG CCG CTA AAA AAG GTG AAA          195
Trp Ser Gly Glu Thr Gly Asn Glu Asp Gln Pro Leu Lys Lys Val Lys
         45                  50                  55

AAA GGT AAC ATT ACG TGG GCC TCT TTT AAC CTC AGC GAA CAG GAC CTT          243
Lys Gly Asn Ile Thr Trp Ala Ser Phe Asn Leu Ser Glu Gln Asp Leu
 60                  65                  70                  75

GAC GAA TAC TAC AAC CAA TTC TCC AAT GCC GTT CTC TGG CCC GCT TTT          291
Asp Glu Tyr Tyr Asn Gln Phe Ser Asn Ala Val Leu Trp Pro Ala Phe
                 80                  85                  90

CAT TAT CGG CTC GAT CTG GTG CAA TTT CAG CGT CCT GCC TGG GAC GGC          339
His Tyr Arg Leu Asp Leu Val Gln Phe Gln Arg Pro Ala Trp Asp Gly
         95                 100                 105

TAT CTA CGC GTA AAT GCG TTG CTG GCA GAT AAA TTA CTG CCG CTG TTG          387
Tyr Leu Arg Val Asn Ala Leu Leu Ala Asp Lys Leu Leu Pro Leu Leu
        110                 115                 120

CAA GAC GAT GAC ATT ATC TGG ATC CAC GAT TAT CAC CTG TTG CCA TTT          435
Gln Asp Asp Asp Ile Ile Trp Ile His Asp Tyr His Leu Leu Pro Phe
125                 130                 135

GCG CAT GAA TTA CGC AAA CGG GGA GTG AAT AAT CGC ATT GGT TTC TTT          483
Ala His Glu Leu Arg Lys Arg Gly Val Asn Asn Arg Ile Gly Phe Phe
140                 145                 150                 155

CTG CAT ATT CCT TTC CCG ACA CCG GAA ATC TTC AAC GCG CTG CCG ACA          531
Leu His Ile Pro Phe Pro Thr Pro Glu Ile Phe Asn Ala Leu Pro Thr
                160                 165                 170

TAT GAC ACC TTG CTT GAA CAG CTT TGT GAT TAT GAT TTG CTG GGT TTC          579
Tyr Asp Thr Leu Leu Glu Gln Leu Cys Asp Tyr Asp Leu Leu Gly Phe
        175                 180                 185

CAG ACA GAA AAC GAT CGT CTG GCG TTC CTG GAT TGT CTT TCT AAC CTG          627
Gln Thr Glu Asn Asp Arg Leu Ala Phe Leu Asp Cys Leu Ser Asn Leu
        190                 195                 200

ACC CGC GTC ACG ACA CGT AGC GCA AAA AGC CAT ACA GCC TGG GGC AAA          675
Thr Arg Val Thr Thr Arg Ser Ala Lys Ser His Thr Ala Trp Gly Lys
205                 210                 215

GCA TTT CGA ACA GAA GTC TAC CCG ATC GGC ATT GAA CCG AAA GAA ATA          723
Ala Phe Arg Thr Glu Val Tyr Pro Ile Gly Ile Glu Pro Lys Glu Ile
220                 225                 230                 235

GCC AAA CAG GCT GCC GGG CCA CTG CCG CCA AAA CTG GCG CAA CTT AAA          771
Ala Lys Gln Ala Ala Gly Pro Leu Pro Pro Lys Leu Ala Gln Leu Lys
                240                 245                 250

GCG GAA CTG AAA AAC GTA CAA AAT ATC TTT TCT GTC GAA CGG CTG GAT          819
Ala Glu Leu Lys Asn Val Gln Asn Ile Phe Ser Val Glu Arg Leu Asp
        255                 260                 265

TAT TCC AAA GGT TTG CCA GAG CGT TTT CTC GCC TAT GAA GCG TTG CTG          867
Tyr Ser Lys Gly Leu Pro Glu Arg Phe Leu Ala Tyr Glu Ala Leu Leu
        270                 275                 280

GAA AAA TAT CCG CAG CAT CAT GGT AAA ATT CGT TAT ACC CAG ATT GCA          915
Glu Lys Tyr Pro Gln His His Gly Lys Ile Arg Tyr Thr Gln Ile Ala
        285                 290                 295

CCA ACG TCG CGT GGT GAT GTG CAA GCC TAT CAG GAT ATT CGT CAT CAG          963
Pro Thr Ser Arg Gly Asp Val Gln Ala Tyr Gln Asp Ile Arg His Gln
300                 305                 310                 315

CTC GAA AAT GAA GCT GGA CGA ATT AAT GGT AAA TAC GGG CAA TTA GGC         1011
Leu Glu Asn Glu Ala Gly Arg Ile Asn Gly Lys Tyr Gly Gln Leu Gly
                320                 325                 330

TGG ACG CCG CTT TAT TAT TTG AAT CAG CAT TTT GAC CGT AAA TTA CTG         1059
Trp Thr Pro Leu Tyr Tyr Leu Asn Gln His Phe Asp Arg Lys Leu Leu
        335                 340                 345

ATG AAA ATA TTC CGC TAC TCT GAC GTG GGC TTA GTG ACG CCA CTG CGT         1107
```

```
Met Lys Ile Phe Arg Tyr Ser Asp Val Gly Leu Val Thr Pro Leu Arg
            350                 355                 360

GAC GGG ATG AAC CTG GTA GCA AAA GAG TAT GTT GCT GCT CAG GAC CCA      1155
Asp Gly Met Asn Leu Val Ala Lys Glu Tyr Val Ala Ala Gln Asp Pro
        365                 370                 375

GCC AAT CCG GGC GTT CTT GTT CTT TCG CAA TTT GCG GGA GCG GCA AAC      1203
Ala Asn Pro Gly Val Leu Val Leu Ser Gln Phe Ala Gly Ala Ala Asn
380                 385                 390                 395

GAG TTA ACG TCG GCG TTA ATT GTT AAC CCC TAC GAT CGT GAC GAA GTT      1251
Glu Leu Thr Ser Ala Leu Ile Val Asn Pro Tyr Asp Arg Asp Glu Val
                400                 405                 410

GCA GCT GCG CTG GAT CGT GCA TTG ACT ATG TCG CTG GCG GAA CGT ATT      1299
Ala Ala Ala Leu Asp Arg Ala Leu Thr Met Ser Leu Ala Glu Arg Ile
            415                 420                 425

TCC CGT CAT GCA GAA ATG CTG GAC GTT ATC GTG AAA AAC GAT ATT AAC      1347
Ser Arg His Ala Glu Met Leu Asp Val Ile Val Lys Asn Asp Ile Asn
        430                 435                 440

CAC TGG CAG GAG TGC TTC ATT AGC GAC CTA AAG CAG ATA GTT CCG CGA      1395
His Trp Gln Glu Cys Phe Ile Ser Asp Leu Lys Gln Ile Val Pro Arg
    445                 450                 455

AGC GCG GAA AGC CAG CAG CGC GAT AAA GTT GCT ACC TTT CCA AAG CTT      1443
Ser Ala Glu Ser Gln Gln Arg Asp Lys Val Ala Thr Phe Pro Lys Leu
460                 465                 470                 475

GCG                                                                   1446
Ala (2) INFORMATION FOR SEQ ID NO: 3:

(i) SEQUENCE CHARACTERISTICS:
        (A) LENGTH: 476 amino acids
        (B) TYPE: amino acid
        (D) TOPOLOGY: linear (ii) MOLECULE TYPE: protein (xi) SEQUENCE DESCRIPTION: SEQ ID NO: 3:

Met Thr Met Ser Arg Leu Val Val Ser Asn Arg Ile Ala Pro Pro
 1               5                  10                  15

Asp Glu His Ala Ala Ser Ala Gly Gly Leu Ala Val Gly Ile Leu Gly
                20                  25                  30

Ala Leu Lys Ala Ala Gly Gly Leu Trp Phe Gly Trp Ser Gly Glu Thr
            35                  40                  45

Gly Asn Glu Asp Gln Pro Leu Lys Lys Val Lys Lys Gly Asn Ile Thr
        50                  55                  60

Trp Ala Ser Phe Asn Leu Ser Glu Gln Asp Leu Asp Glu Tyr Tyr Asn
65                  70                  75                  80

Gln Phe Ser Asn Ala Val Leu Trp Pro Ala Phe His Tyr Arg Leu Asp
                85                  90                  95

Leu Val Gln Phe Gln Arg Pro Ala Trp Asp Gly Tyr Leu Arg Val Asn
                100                 105                 110

Ala Leu Leu Ala Asp Lys Leu Leu Pro Leu Leu Gln Asp Asp Asp Ile
            115                 120                 125

Ile Trp Ile His Asp Tyr His Leu Leu Pro Phe Ala His Glu Leu Arg
        130                 135                 140

Lys Arg Gly Val Asn Asn Arg Ile Gly Phe Phe Leu His Ile Pro Phe
145                 150                 155                 160

Pro Thr Pro Glu Ile Phe Asn Ala Leu Pro Thr Tyr Asp Thr Leu Leu
                165                 170                 175

Glu Gln Leu Cys Asp Tyr Asp Leu Leu Gly Phe Gln Thr Glu Asn Asp
```

```
                    180                 185                 190
Arg Leu Ala Phe Leu Asp Cys Leu Ser Asn Leu Thr Arg Val Thr Thr
            195                 200                 205
Arg Ser Ala Lys Ser His Thr Ala Trp Gly Lys Ala Phe Arg Thr Glu
    210                 215                 220
Val Tyr Pro Ile Gly Ile Glu Pro Lys Glu Ile Ala Lys Gln Ala Ala
225                 230                 235                 240
Gly Pro Leu Pro Pro Lys Leu Ala Gln Leu Lys Ala Glu Leu Lys Asn
                245                 250                 255
Val Gln Asn Ile Phe Ser Val Glu Arg Leu Asp Tyr Ser Lys Gly Leu
            260                 265                 270
Pro Glu Arg Phe Leu Ala Tyr Glu Ala Leu Leu Glu Lys Tyr Pro Gln
        275                 280                 285
His His Gly Lys Ile Arg Tyr Thr Gln Ile Ala Pro Thr Ser Arg Gly
    290                 295                 300
Asp Val Gln Ala Tyr Gln Asp Ile Arg His Gln Leu Glu Asn Glu Ala
305                 310                 315                 320
Gly Arg Ile Asn Gly Lys Tyr Gly Gln Leu Gly Trp Thr Pro Leu Tyr
                325                 330                 335
Tyr Leu Asn Gln His Phe Asp Arg Lys Leu Leu Met Lys Ile Phe Arg
            340                 345                 350
Tyr Ser Asp Val Gly Leu Val Thr Pro Leu Arg Asp Gly Met Asn Leu
        355                 360                 365
Val Ala Lys Glu Tyr Val Ala Ala Gln Asp Pro Ala Asn Pro Gly Val
    370                 375                 380
Leu Val Leu Ser Gln Phe Ala Gly Ala Ala Asn Glu Leu Thr Ser Ala
385                 390                 395                 400
Leu Ile Val Asn Pro Tyr Asp Arg Asp Glu Val Ala Ala Ala Leu Asp
                405                 410                 415
Arg Ala Leu Thr Met Ser Leu Ala Glu Arg Ile Ser Arg His Ala Glu
            420                 425                 430
Met Leu Asp Val Ile Val Lys Asn Asp Ile Asn His Trp Gln Glu Cys
        435                 440                 445
Phe Ile Ser Asp Leu Lys Gln Ile Val Pro Arg Ser Ala Glu Ser Gln
    450                 455                 460
Gln Arg Asp Lys Val Ala Thr Phe Pro Lys Leu Ala
465                 470                 475

(2) INFORMATION FOR SEQ ID NO: 4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 4:

TCCCCATGGA ATCAAAGCAT CC                                            22

(2) INFORMATION FOR SEQ ID NO: 5:

(i) SEQUENCE CHARACTERISTICS:
        (A) LENGTH: 22 base pairs
        (B) TYPE: nucleic acid
        (C) STRANDEDNESS: single
```

(D) TOPOLOGY: linear (ii) MOLECULE TYPE: cDNA (iii) HYPOTHETICAL: YES (xi) SEQUENCE DESCRIPTION: SEQ ID NO: 5:

GATTGGATCC AGGGCACGGC TG                                                22

(2) INFORMATION FOR SEQ ID NO: 6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 6:

CTAGGTCGTG ATTCTGATAC AGGTGGCCAG GTG                                    33

(2) INFORMATION FOR SEQ ID NO: 7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO: 7:

CAGCATCGGC ATAGTGCCCA TGTATCACGT AAGGC                                  35

(2) INFORMATION FOR SEQ ID NO: 8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 8:

AGCTCACGAG CTCTCAGG                                                     18

(2) INFORMATION FOR SEQ ID NO: 9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 9:

AGCTCCTGAG AGCTCGTG                                                     18

(2) INFORMATION FOR SEQ ID NO: 10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 10:

GATCCCCCGG GGCATGCAAG CTTG                                              24

(2) INFORMATION FOR SEQ ID NO: 11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 11:

GATCCAAGCT TGCATGCCCC GGGG                                              24

(2) INFORMATION FOR SEQ ID NO: 12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 12:

GAGAAAATAC CCGGGGTGAT GAC                                               23

(2) INFORMATION FOR SEQ ID NO: 13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 13:

GATAATCGTG GATCCAGATA ATGTC                                             25

(2) INFORMATION FOR SEQ ID NO: 14:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 14:

```
GATCGTCAGA TCTAGC                                                    16

(2) INFORMATION FOR SEQ ID NO: 15:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 15:

AATTGCTAGA TCTGAC                                                    16

(2) INFORMATION FOR SEQ ID NO: 16:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 16:

AGCTTCCCCC CCG                                                       13

(2) INFORMATION FOR SEQ ID NO: 17:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 17:

AATTCGGGGG GGA                                                       13

(2) INFORMATION FOR SEQ ID NO: 18:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 18:

GTTTCTACAG GACGGAGGAT CCTGGAAGTA TTTGAAAGA                            39

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

```
        (ii) MOLECULE TYPE: cDNA (iii) HYPOTHETICAL: YES (xi) SEQUENCE DESCRIPTION: SEQ ID NO: 19:

CAGCTATGAC CATGATTACG                                                     20

(2) INFORMATION FOR SEQ ID NO: 20:

(i) SEQUENCE CHARACTERISTICS:
             (A) LENGTH: 34 base pairs
             (B) TYPE: nucleic acid
             (C) STRANDEDNESS: single
             (D) TOPOLOGY: linear (ii) MOLECULE TYPE: cDNA (iii) HYPOTHETICAL: YES (xi) SEQUENCE DESCRIPTION: SEQ ID NO: 20:

AGCTGGCGTG AGGAGCGGTT AATAAGCTTG AGCT                                     34

(2) INFORMATION FOR SEQ ID NO: 21:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: cDNA (iii) HYPOTHETICAL: YES (xi) SEQUENCE DESCRIPTION: SEQ ID NO: 21:

CAAGCTTATT AACCGCTCCT CACGCC                                              26
```

PRODUCTION OF TREHALOSE IN PLANTS

FIELD OF THE INVENTION

This invention relates to the modification of plant carbohydrate metabolism using recombinant DNA techniques, recombinant DNA for use therein, as well as plants and parts of plants having a modified genetic constitution. Said plants may be used to extract specific carbohydrate compounds, or alternatively, they may be processed as food, feed, or ingredients thereof, having improved properties due to the presence of said carbohydrate compounds, e.g. during processing.

STATE OF THE ART

Trehalose is a general name given to D-glucosyl D-glucosides which comprise disaccharides based on two α-,α,β- and β,β-linked glucose molecules. Trehalose, and especially α-trehalose 1-(O-a-D-glucopyranosyl)-1'-O-α-D-glucopyranose) is a widespread naturally occurring disaccharide.

The chemical synthesis of trehalose is difficult (protecting groups required) and inefficient. Current natural sources of trehalose are mushrooms and the yeast *Saccharomyces cerevisiae*, that can accumulate over 10% of dry weight as trehalose. However production is hampered by high trehalase activity causing rapid metabolization of trehalose. Elbein A. D. (1974, Adv. Carbohydrate Chem. and Biochem. 30, 227–256) gives a review of the occurrence and metabolism of the disaccharide trehalose, particularly α,α-trehalose, in living organisms. In plants, the presence of trehalose has been reported in some lower plant species, as well as in a number of higher plant species belonging to the *spermatophyta; Echinops persious, Carex brunescens; Fagus silvaticus*. However, these results have never been firmly established by other authors (e.g. Kendall et al., 1990, Phytochemistry 29, No. 8, 2525–2528). For instance, Kendall et al, supra, referring to the occurrence of trehalose in spermatophytes, stated that the presence thereof has only been firmly documented for caraway seed (*Carum caryi*). A report of the presence of trehalose in sunflower by Cegla et al., (1977, J. Am. Oil Chem. Soc. 54, 150 et seq.) was questioned by Kandler et al., (in: *The Biochemistry of Plants* Vol. 3 Carbohydrates: Structure and Function; Preiss, J., ed., p. 228. Academic Press) according to Kendall et al, 1990, supra. Reports of trehalose in beech (*Fagus sylvaticus*) and cabbage could not be verified by other authors (Kendall et al., 1990, supra, and references therein).

In spite of the apparent rarity of trehalose in higher plants, the presence of trehalose degrading activities was reported for a significant number of the investigated plant families. Stable high trehalase activity was found in three wheat lines, jack pine, and *Selaginella lepidophylla*. Stable, low trehalase activity was found in alfalfa, black Mexican sweet corn and white spruce. Labile, moderate activities were found in two different suspensions of canola, but these could probably not be ascribed to specific trehalase activity. Barley, brome grass, soybean and black spruce were reported to contain no trehalase activity at all (Kendall, 1990, supra).

In organisms capable of its production, trehalose is believed to be biosynthesized as the 6-phosphate, whereas the storage form is the free sugar. It is therefore believed, that organisms that produce and/or store trehalose contain a phosphatase capable of cleaving trehalose 6-phosphate (Elbein, 1974, supra). Little is known about the presence of specific trehalose phosphate phosphatases in higher plants.

International patent application WO93/17093 A1, published on Sep. 2, 1993, describes the production of trehalose in yeast transgenic for yeast genes coding for trehalose phosphate synthase. It was suggested that trehalose may be produced in higher plants as well, using these yeast genes, but there is no actual disclosure of trehalose production in a plant. It is to be noted that WO93/17093 A1 was published prior to the filing date but subsequent to the priority date of the instant application.

SUMMARY OF THE INVENTION

The present invention provides for a method for the production of trehalose in a plant host due to the presence in said plant host of a plant expressible gene which comprises in sequence:
 (a) a transcriptional initiation region that is functional in said plant host,
 (b) a DNA sequence encoding a trehalose phosphate synthase activity, and optionally
 (c) a transcriptional termination sequence that is functional in said plant host.

Another embodiment of the invention comprises the production of trehalose in a plant host due to the presence in said plant host of a plant expressible gene which comprises in sequence:
 (d) a transcriptional initiation region that is functional in said plant host,
 (e) a DNA sequence encoding a trehalose phosphate synthase activity, and optionally
 (f) a transcriptional termination sequence that is functional in said plant host, and
 a plant expressible gene comprising in sequence:
  (a) a transcriptional initiation region that is functional in said plant host,
  (b) a DNA sequence encoding an RNA sequence which is at least partially complementary to an RNA sequence which encodes a sucrose phosphate synthase enzyme naturally (SPS) occurring in said plant host, and optionally
  (c) a transcriptional termination sequence that is functional in said plant host, Yet another embodiment of the invention comprises the production of trehalose in a plant host due to the presence in said plant host of a plant expressible gene which comprises in sequence:
 (d) a transcriptional initiation region that is functional in said plant host,
 (e) a DNA sequence encoding a trehalose phosphate synthase activity, and optionally
 (f) a transcriptional termination sequence that is functional in said plant host, and
 a plant expressible gene comprising in sequence:
  (a) a transcriptional initiation region that is functional in said plant host,
  (b) a DNA sequence encoding an RNA sequence which is at least partially complementary to an RNA sequence which encodes an ADP-glucose pyrophosphorylase enzyme naturally occuring in said plant host, and optionally
  (c) a transcriptional termination sequence that is functional in said plant host.

Yet another embodiment of the invention comprises the production of trehalose in a plant host due to the presence in said plant host of a plant expressible gene which comprises in sequence:

(a) a transcriptional initiation region that is functional in said plant host,
(b) a DNA sequence encoding a trehalose phosphate synthase activity, and optionally
(c) a transcriptional termination sequence that is functional in said plant host,
and a plant expressible gene comprising in sequence:
(d) a transcriptional initiation region that is functional in said plant host,
(e) a DNA sequence encoding an RNA sequence at least partially complementary to an RNA sequence which encodes a sucrose phosphate synthase enzyme naturally occurring in said plant host, and optionally
(f) a transcriptional termination sequence that is functional in said plant host,
and a plant expressible gene comprising in sequence:
(g) a transcriptional initiation region that is functional in said plant host,
(h) a DNA sequence encoding an RNA sequence at least partially complementary to an RNA sequence which encodes an ADP-glucose pyrophosphorylase enzyme naturally occurring in said plant host, and optionally
(i) a transcriptional termination sequence that is functional in said plant host.

The invention also extends to the plant expressible genes used in the process for making trehalose, as well as to the combinations of plant expressible genes, as well as to cloning plasmids, transformation vectors, microorganisms, an individual plant cells harboring plant expressible genes according to the invention.

The invention also provides a recombinant plant DNA genome which contains a plant expressible trehalose phosphate synthase gene that is not naturally present therein. The invention also comprises a recombinant plant DNA genome which comprises a plant expressible trehalose phosphate synthase gene that is not naturally present therein and in addition a plant expressible gene capable of inhibiting biosynthesis of an SPS activity, and/or a plant expressible gene capable of inhibiting biosynthesis of an AGPase activity.

The invention also provides a method for obtaining a plant capable of producing trehalose comprising the steps of,
(1) introducing into a recipient plant cell a plant expressible gene comprising in sequence:
  (a) a transcriptional initiation region that is functional in said plant host,
  (b) a DNA sequence encoding a trehalose phosphate synthase activity,
  (c) a transcriptional termination sequence that is functional in said plant host, and a plant expressible gene comprising in sequence:
  (d) a transcriptional initiation region that is functional in said plant host,
  (e) a DNA sequence encoding a selectable marker gene that is functional in said plant host, and optionally
  (f) a transcriptional termination sequence that is functional in said plant host,
(2) generating a plant from a transformed cell under conditions that allow for selection for the presence of the selectable marker gene.

The invention also comprises plants which produce (increased levels of) trehalose as a result of genetic modification.

The invention further comprises plants having a recombinant DNA genome containing a plant expressible gene according to the invention.

The invention also comprises plants having a recombinant DNA genome containing a plant expressible gene according to the invention and which plants produce trehalose.

The invention also comprises plants having a recombinant DNA genome according to the invention and which exhibit increased drought resistance.

The invention also extends to parts of plants according to the invention such as cells or protoplasts or cultures thereof, flowers, fruits, leaves, pollen, roots (including hairy root cultures), seeds, stalks, tubers (including so-called microtubers) and the like.

The invention also extends to a method of preserving plants or plant parts in the presence of trehalose comprising the steps of:
(1) growing a plant according to the invention which produces trehalose,
(2) harvesting the plant or plant parts which contain trehalose, and
(3) air drying the plants or plant parts or alternatively,
(4) freeze drying the plants or plant parts.

The invention further comprises the plants and plant parts which have been preserved by a method according to the invention.

The invention also includes a method for the production of trehalose comprising the steps of:
(1) growing a plant which by virtue of a recombinant plant DNA genome is capable of producing (increased levels of) trehalose,
(2) harvesting said plant or plant part,
(3) isolating the trehalose from the said plant or the said plant part.

The invention further includes a method for the production of trehalose comprising the steps of:
(1) growing in culture plant cells which by virtue of a recombinant plant DNA genome are capable of producing (increased levels of) trehalose,
(2) isolating the trehalose from the said plant cell culture.

The invention further provides an isolated nucleic acid sequence encoding a trehalose phosphate synthase activity. A preferred isolated nucleic acid sequence is one obtained from *E. coli*, still more preferred is the isolated nucleic acid sequence represented in SEQ ID NO: 2. Another preferred embodiment comprises a nucleic acid sequence that codes for an amino acid sequence as in SEQ ID NO: 3.

The following figures further illustrate the invention.

DESCRIPTION OF THE FIGURES

FIG. 2. Schematic map of the EMBL4clone 7F11 from Kohara et al. (1987), containing the otsBA operon from *E. coli*. The 18.8 kb insert has been shaded. The restriction sites for the enzymes EcoRV and HindIII used to clone the otsA gene are indicated, as well as their distance in kb with respect to the left-hand site of the insert. The otsA and B gene are indicated, the arrows shows the direction of transcription. (See FIG. 8, extended map).

FIG. 3. Sequence of the cloned potato SPS cDNA. Underscore: maize SPS cDNA sequences used as oligonucleotides in the PCR amplification reaction.

FIG. 8. Extended map of the EMBL4clone 7F11 from Kohara et al. (1987), containing the otsBA operon from *E.coli*. The location of the TPS open reading frame (ORF) is indicated. (*: HindIII sites not present in the map of Kohara et al., infra)

DETAILED DESCRIPTION OF THE INVENTION

A preferred embodiment of the invention comprises a potato plant capable of producing trehalose in tubers due to the presence in said potato plant of a plant expressible gene which comprises in sequence:

(a) a transcriptional initiation region derived from the 35S RNA of CaMV flanked upstream by a double enhancer, (b) a DNA sequence encoding trehalose phosphate synthase which is the coding region of the ptaA gene located in the otsBA operon of *E. coli*, (c) a transcriptional-termination sequence derived from the nopaline synthase (nos) gene of Agrobacterium. Tubers of transgenic plants containing the plant expressible TPS gene produced trehalose, whereas control plants lacking this gene did not. Apparently, the trehalose phosphate which is produced by the transgenic tubers is converted into trehalose. Apparently, it is not required to provide for a trehalose phosphate phosphatase activity since it seems present in potato.

Figure 1:
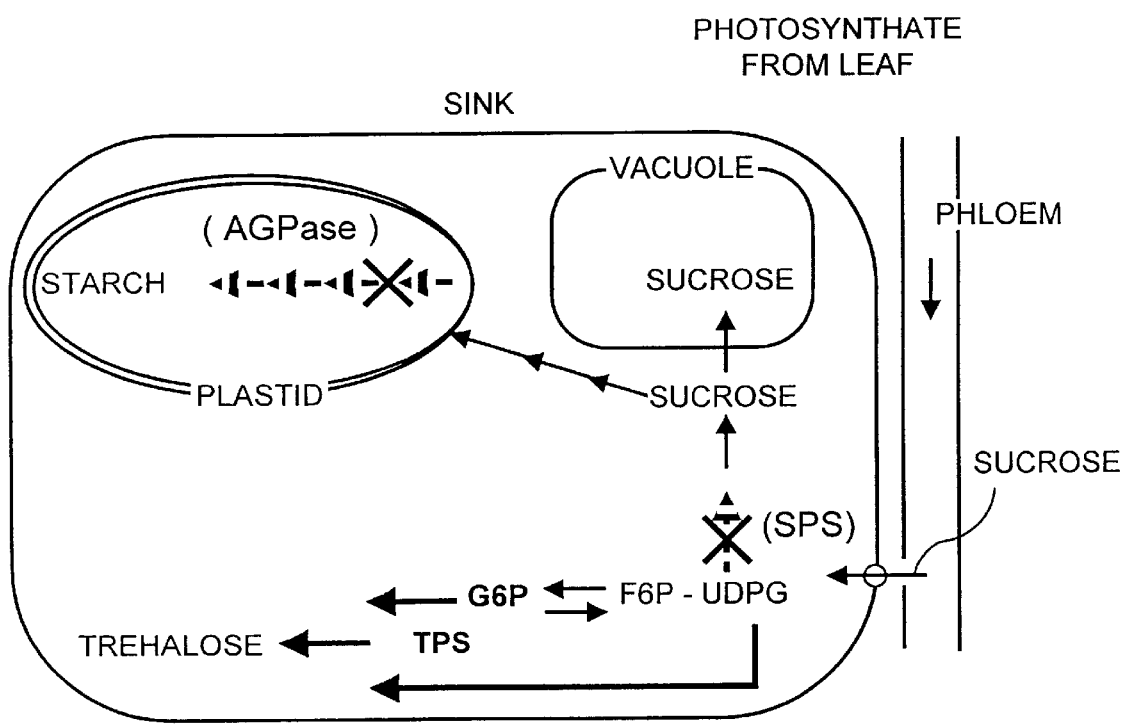
FIG. 1. Schematic representation of parts of the sucrose and starch biosynthetic pathways in plant sink tissues. The figure shows that carbohydrate produced in the leaf by photosynthesis is transported via the phloem tissue in the form of sucrose. Upon entering the sink it is unloaded by a membrane bound invertase activity to yield the monosugars glucose and fructose. By the action of a number of enzymatic steps these monosugars are converted to starch and/or sucrose as roughly shown here. The glucose metabolites G6P and UDPG are believed to be used as the substrates for the TPS-enzyme engineered into the plant by introduction of the plant expressible otsA gene. The figure shows how the amount of UDPG and G6P available as substrate is increased by reducing the levels of the enzymes SPS and AGPase. Their inhibition is marked with a cross.

Also illustrated in FIG. 1 is an approach to improve substrate availability for TPS. To this end two genes influencing the availability of glucose-6 phosphate (G6P) and UDPG, to with an antisense SPS gene and a antisense APGase have been cloned under the control of the CaMV 35S promoter for expression in plant hosts. If introduced into a plant host containing a plant expressible TPS gene according to the invention, this will increase substrate availability for TPS and therefore trehalose synthesis. It will readily occur to someone skilled in the art that also other antisense genes may be used to block the synthesis of sucrose or starch, in order to improve substrate availability.

Although the invention is described in detail for potato plants which express a plant expressible trehalose phosphate synthase gene from *E. coli* under the control of the CaMV 35S promoter as transcription initiation region, it will be clear to those of skill in the art that other spermatophytic plant hosts are equally suitable for the production of trehalose. Preferred plant hosts among the *spermatophyta* are the Angiospermae, notably the Dicotyledoneae, comprising inter alia the Solanaceae as a representative family, and the Monocotyledoneae, comprising inter alia the Gramineae as a representative family. Suitable host plants, as defined in the context of the present invention include plants (as well as parts and cells of said plants) and their progeny which have been genetically modified using recombinant DNA techniques to cause or enhance production of trehalose interest in the desired plant or plant organ; these plants may be used directly (e.g. the plant species which produce edible parts) or after the trehalose is purified from said host (which be from edible as well as inedible plant hosts). Crops with edible parts according to the invention include those which have flowers such as cauliflower (*Brassica oleracea*), artichoke (*Cynara scolymus*), fruits such as apple (Malus, e.g. *domesticus*), banana (Musa, e.g. acuminata), berries (such as the currant, Ribes, e.g. rubrum), cherries (such as the sweet cherry, Prunus, e.g. *avium*), cucumber (Cucumis, e.g. *sativus*), grape (Vitis, e.g. *vinifera*), lemon (*Citrus limon*), melon (*Cucumis melo*), nuts (such as the walnut, Juglans, e.g. regia; peanut, *Arachis hypogeae*), orange (Citrus, e.g. *maxima*), peach (Prunus, e.g. *persica*), pear (Pyra, e.g. *communis*), pepper (Solanum, e.g. *capsicum*), plum (Prunus, e.g. *domestica*), strawberry (Fragaria, e.g. *moschata*), tomato (Lycopersicon, e.g. *esculentum*), leafs, such as alfalfa (*Medicago sativa*), cabbages (such as *Brassica oleracea*), endive (*Cichoreum*, e.g. *endivia*), leek (*Allium porrum*), lettuce (*Lactuca sativa*), spinach (Spinaciaololeraceae), tobacco (*Nicotiana tabacum*) roots, such as arrowroot (*Maranta arundinacea*), beet (*Beta vulgaris*), carrot (*Daucus carota*), cassava (*Manihot esculenta*), turnip (*Brassica rapa*), radish (*Baphanus sativus*), yam (*Dioscorea esculenta*), sweet potato (*Ipomoea batatas*) and seeds, such as bean (*Phaseolus vulgaris*), pea (*Pisum sativum*), soybean (*Glycin max*), wheat (*Triticum aestivum*), barley (*Hordeum vulgare*), corn (*Zea mays*), rice (*Oryza sativa*), tubers, such as kohlrabi (*Brassica oleraceae*), potato (*Solanum tuberosum*), and the like. The edible parts may be conserved by drying in the presence of enhanced trehalose levels produced therein due to the presence of a plant expressible trehalose phosphate synthase gene. It may be advantageous to produce enhanced levels of trehalose, by putting the DNA encoding the TPS activity under the control of a plant-organ or tissue-specific promoter; the choice of which can readily be determined by those of skill in the art.

Any trehalose phosphate synthase gene under the control of regulatory elements necessary for expression of DNA in plant cells, either specifically or constitutively, may be used, as long as it is capable of producing an active trehalose phosphate synthase activity. The nucleic acid sequence represented in SEQ ID NO: 2, in fact any open reading frame encoding a trehalose phosphate synthase activity according to the invention, may be altered without necessarily altering the amino acid sequence of the protein encoded thereby. This fact is caused by the degeneracy of the genetic code. Thus the open reading frame encoding the trehalose phosphate synthase activity may be adapted to codon usage in the host plant of choice.

Also the isolated nucleic acid sequence represented by SEQ ID NO: 2, may be used to identify trehalose phosphate synthase activities in other organisms and subsequently isolating them, by hybridising DNA from other sources with a DNA- or RNA fragment obtainable from the *E.coli* gene.

Preferably, such DNA sequences are screened by hybridising under stringent conditions (such as temperature and ionic strength of the hybridisation mixture). Whether or not conditions are stringent also depends on the nature of the hybridisation, i.e. DNA:DNA, DNA:RNA, RNA:RNA, as well as the length of the shortest hybridising fragment. Those of skill in the art are readily capable of establishing a stringent hybridisation regime.

Sources for isolating trehalose phosphate synthase activities include microorganisms (e.g. bacteria, yeast, fungi), plants, animals, and the like. Isolated DNA sequences encoding trehalose phosphate activity from other sources may be used likewise in a method for producing trehalose according to the invention.

The invention also encompasses nucleic acid sequences which have been obtained by modifying the nucleic acid sequence represented in SEQ ID NO: 2 by mutating one or more codons so that it results in amino acid changes in the encoded protein, as long as mutation of the amino acid sequence does not entirely abolish trehalose phosphate synthase activity.

In principle any plant host is suitable in combination with any plant expressible trehalose phosphate synthase gene. As trehalose genes from other sources become available these can be used in a similar way to obtain a plant expressible trehalose phosphate synthase gene combination as described here.

The inhibition of endogenous genes in order to enhance substrate availability for the trehalose phosphate synthase, as exemplified herein with the inhibition of endogenous sucrose phosphate synthase gene and the ADP-Glucose pyrophosphorylase gene, may be conducted in a number of ways the choice of which is not critical to the invention. Preferably gene inhibition is achieved through the so-called 'antisense approach'. Herein a DNA sequence is expressed which produces an RNA that is at least partially complementary to the RNA which encodes the enzymatic activity that is to be blocked e.g. AGP-ase or SPS, in the examples). It is preferred to use homologous antisense genes as these are more efficient than heterologous genes. The isolation of an antisense SPS gene from potato using a maize SPS-gene sequence as probe serves to illustrate the feasibility of this strategy. It is not meant to indicate that, for practicing the invention the use of homologous antisense fragments is required. An alternative method to block the synthesis of undesired enzymatic activities is the introduction into the genome of the plant host of an additional copy of an endogenous gene present in the plant host. It is often observed that such an additional copy of a gene silences the endogenous gene: this effect is referred to in the literature as the co-suppressive effect, or co-suppression. In principle both dicotyledonous and monocotyledonous plants that are amenable for transformation, can be modified by introducing a plant expressible gene according to the invention into a recipient cell and growing a new plant that harbors and expresses the plant expressible gene. Preferred plants according to the invention are those that are capable of converting trehalose-phosphate into trehalose, and which do contain no or little trehalose degrading activity. It will be understood that plants that lack the ability to convert the trehalose phosphate into trehalose are also included in the present invention. These plants may be further modified by introducing additional genes that encode phosphatases that are capable of the conversion of trehalose phosphate into trehalose. In principle also plants are envisaged that contain trehalases, since these plants can be made suitable for the production of trehalose by inhibiting the activity of such enzymes, for instance by inhibiting expression of the genes encoding such enzymes using the antisense approach.

The method of introducing the plant expressible trehalosephosphate synthase gene into a recipient plant cell is not crucial, as long as the gene is stably incorporated into the genome of said plant cell. In addition to the use of strains of the genus Agrobacterium various other techniques are available for the introduction of DNA into plant cells, such as transformation of protoplasts using the calcium/polyethylene glycol method, electroporation and microinjection or (coated) particle bombardment (Potrykus, 1990, Bio/Technol. 8, 535–542).

In addition to these so-called direct DNA transformation methods, transformation systems involving vectors are widely available, such as viral vectors (e.g. from the Cauliflower Mosaic Virus (CaMV) and bacterial vectors (e.g. from the genus Agrobacterium) (Potrykus, 1990, Bio/Technol. 8, 535–542). After selection and/or screening, the protoplasts, cells or plant parts that have been transformed can be regenerated into whole plants, using methods known in the art (Horsch et al. 1985, Science 225, 1229–1231).

It has been shown that monbcotyladonous plants are amenable to transformation and that fertile transgenic plants can be regenerated from transformed cells. The development of reproducible tissue culture systems for these crops, together with the powerful methods for introduction of genetic material into plant cells has facilitated transformation. Presently, preferred methods for transformation of monocots are microprojectile bombardment of explants or suspension cells, and direct DNA uptake or electroporation (Shimamoto, et al, 1989, Nature 338, 274–276). Transgenic maize plants have been obtained by introducing the *Streptomycea hygroscopicus* bar-gene, which encodes phosphinothricin acetyltransferase (an enzyme which inactivates the herbicide phosphinothricin), into embryogenic cells of a maize suspension culture by microprojectile bombardment (Gordon-Kamm, 1990, Plant Cell, 2, 603–618). The introduction of genetic material into aleurone protoplasts of other monocot crops such as wheat and barley has been reported (Lee, 1989, Plant Mol. Biol. 13, 21–30). Wheat plants have been regenerated from embryogenic suspension culture by selecting only the aged compact and nodular embryogenic callus tissues for the establishment of the embryogenic suspension cultures (Vasil, 1990 Bio/Technol. 8, 429–434). The combination with transformation systems for these crops enables the application of the present invention to monocots. These methods may also be applied for the transformation and regeneration of dicots.

Monocotyledonous plants, including commercially important crops such as corn are amenable to DNA transfer by Agrobacterium strains (European patent 159 418 B1; Gould J, Michael D, Hasegawa O, Ulian E C, Peterson G, Smith R H, (1991) Plant. Physiol. 95, 426–434).

As regards the choice of the host plant it is preferred to select plant species with little or no trehalose degrading activity. However, plants that do exhibit trehalase activity are not excluded from being a suitable host plant for the production of trehalose, although it may be necessary to provide for inhibition of trehalase activity if this prevents the accumulation of trehalose altogether. Such inhibition can be achieved using the antisense approach well known in the art, and illustrated for other purposes in this specification.

It should also be understood that the invention is not limited to the use of the CaMV 35S promoter as transcription initiation region. Suitable DNA sequences for control of expression of the plant expressible genes, including marker genes, such as transcriptional initiation regions, enhancers, non-transcribed leaders and the like, may be derived from any gene that is expressed in a plant cell which, such as endogenous plant genes, genes naturally expressed in plant cells such as those located on wild-type T-DNA of Agrobacterium, genes of plant viruses, as well as other eukaryotic genes that include a transcription initiation region that conforms to the consensus sequence for eukaryotic transcription initiation. Also intended are hybrid promoters combining functional portions of various promoters, or synthetic equivalents thereof. Apart from constitutive promoters, inducible promoters, or promoters otherwise regulated in their expression pattern, e.g. developmentally or cell-type specific, may be used to control expression of the plant expressible genes according to the invention as long as they are expressed in plant parts that contain substrate for TPS.

To select or screen for transformed cells, it is preferred to include a marker gene linked to the plant expressible gene according to the invention to be transferred to a plant cell. The choice of a suitable marker gene in plant transformation is well within the scope of the average skilled worker; some examples of routinely used marker genes are the neomycin phosphotransferase genes conferring resistance to kanamycin (EP-B 131 623), the Glutathion-S-transferase gene from rat liver conferring resistance to glutathione derived herbicides (EP-A 256 223), glutamine synthetase conferring upon overexpression resistance to glutamine synthetase inhibitors such as phosphinothricin (WO87/05327), the acetyl transferase gene from Streptomyces viridochromogenes conferring resistance to the selective agent phosphinothricin (EP-A 275 957), the gene encoding a 5-enolshikimate-3-phosphate synthase (EPSPS) conferring tolerance to N-phosphonomethylglycine, the bar gene conferring resistance against Bialaphos (e.g. WO91/02071) and the like. The actual choice of the marker is not crucial as long as it is functional (i.e. selective) in combination with the plant cells of choice.

The marker gene and the gene of interest do not have to be linked, since co-transformation of unlinked genes (U.S. Pat. No. 4,399,216) is also an efficient proces in plant transformation.

Preferred plant material for transformation, especially for dicotyledonous crops are leaf-discs which can be readily transformed and have good regenerative capability (Horsch R. B. at al., (1985) Science 227, 1229–1231).

Whereas the production of trehalose can be achieved with the plant expressible trehalose phosphate synthase gene as the sole carbohydrate modifying gene, the invention is further illustrated with examples of additional plant expressible antisense genes that are capable of effecting an increase of the availability of the substrate for trehalose phosphate synthase. Specific examples of such genes are the plant expressible antisense genes for SPS from maize and potato and AGPase from potato. The down regulation of carbohydrate modifying enzymes using the antisense approach is not limited by the specific examples. For instance partially complementary plant expressible antisense genes can be used to inhibit expression of a target gene, as long as the plant expressible antisense gene produces a transcript that is sufficiently complementary with the transcript of the target gene and sufficiently long to inhibit expression said target gene.

It is immaterial to the invention how the presence of two or more genes in the same plant is effected. This can inter alia done be achieved by one of the following methods:

(a) transformation of the plant line with a multigene construct containing more than one gene to be introduced, (b) co-transforming different constructs to the same plant line simultaneously, (c) subsequent rounds of transformation of the same plant with the genes to be introduced, (d) crossing two plants each of which contains a different gene to be introduced into the same plant.

The field of application of the invention lies both in agriculture and horticulture, for instance due to improved properties of the modified plants as such, as well as in any form of industry where trehalose is or will be applied. Trehalose phosphate and trehalose can be used as such for instance in purified form or in admixtures, or in the form of a storage product in plant parts. Plant parts harboring (increased levels of) trehalose phosphate or trehalose may be used as such or processed without the need to add trehalose.

Also trehalose can be purified from the plants or plant parts producing it and subsequently used in an industrial process. In the food industries trehalose can be employed by adding trehalose to foods before drying. Drying of foods is an important method of preservation in the industry. Trehalose seems especially useful to conserve food products through conventional air-drying, and to allow for fast reconstitution upon addition of water of a high quality product (Roser et al, July 1991, Trends in Food Science and Technology, pp. 166–169). The benefits include retention of natural flavors/fragrances, taste of fresh product, and nutritional value (proteins and vitamins). It has been shown that trehalose has the ability to stabilize proteins and membranes, and to form a chemically inert, stable glass. The low water activity of such thoroughly dried food products prevents chemical reactions, that could cause spoilage.

Field crops like corn, cassava, potato, sugar beet and sugarcane have since long been used as a natural source for bulk carbohydrate production (starches and sucrose). The production of rehalose in such crops, facilitated by genetic engineering of the rehalose-biosynthetic pathway into these plant species, would allow the exploitation of such engineered crops for trehalose production.

All references cited in this specification are indicative of he level of skill in the arts to which the invention pertains. All publications, whether patents or otherwise, referred to previously or later in this specification are herein incorporated by reference as if each of them was individually incorporated by reference.

The Examples given below are just given for purposes of enablement and do not intend in any way to limit the scope of the invention.

EXPERIMENTAL

DNA manipulations

All DNA procedures (DNA isolation from *E.coli*, restriction, ligation, transformation, etc.) are performed according to standard protocols (Sambrook et al. (1989) Molecular Cloning: a laboratory manual, 2nd ed. Cold Spring Harbor Laboratory Press, CSH, New York).

Strains

In all examples *E.coli* K-12 strain DH5α is used for cloning. The Agrobacterium tumefaciens strain used for plant transformation experiments is MOG101 which is a non-oncogenic octopine type helper strain derived from LBA1010 (Koekman et al. (1982) Plasmid 7, 119) by substitution of the T-DNA by a spectinomycin resistance marker.

Construction of Agrobacterium strain MOG101

A binary vector system (Hoekema A., Hirsch, P. R., Hooykaas, P. J. J., and Schilperoort, R. A. (1983) Nature 303, 179) is used to transfer gene constructs into potato and tobacco plants. The helper plasmid conferring the *Agrobactrium tumefaciens* virulence functions is derived from the octopine Ti-plasmid pTiB6. MOG101 is an *Agrobacterium tumefaciens* strain carrying a non-oncogenic Ti-plasmid (Koekman et. al. 1982, supra) from which the entire T-region is deleted and substituted by a bacterial Spectinomycin resistance marker from transposon Tn1831 (Hooykaas et al., 1980 Plasmid 4, 64–75).

Figure 5:
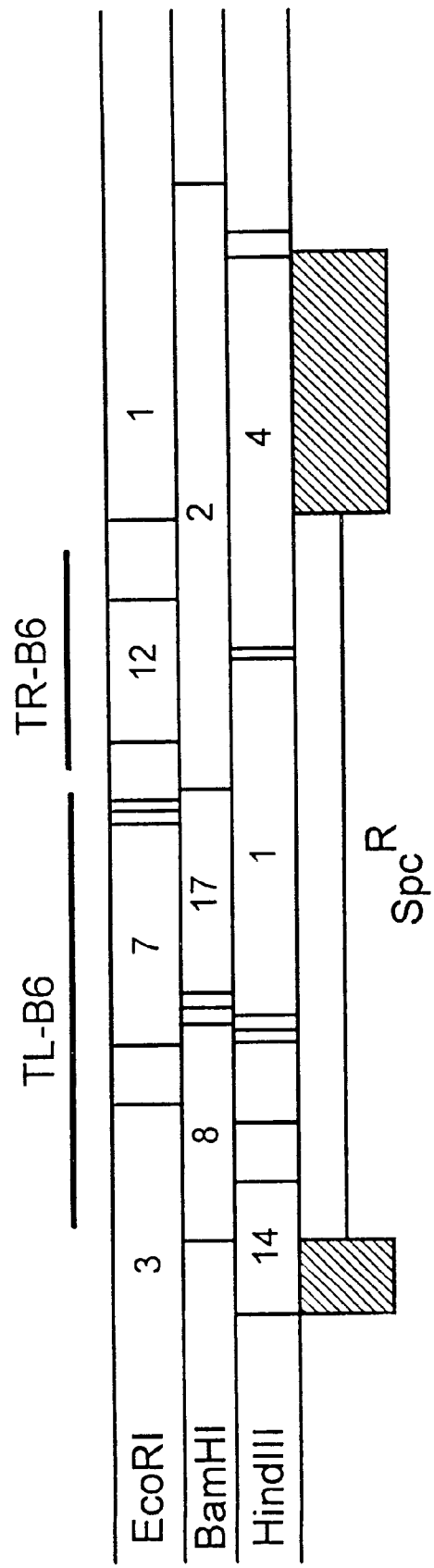
FIG. 5. Restriction map of part of pTiB6 showing two fragments cloned in pMOG579.
Figure 6:
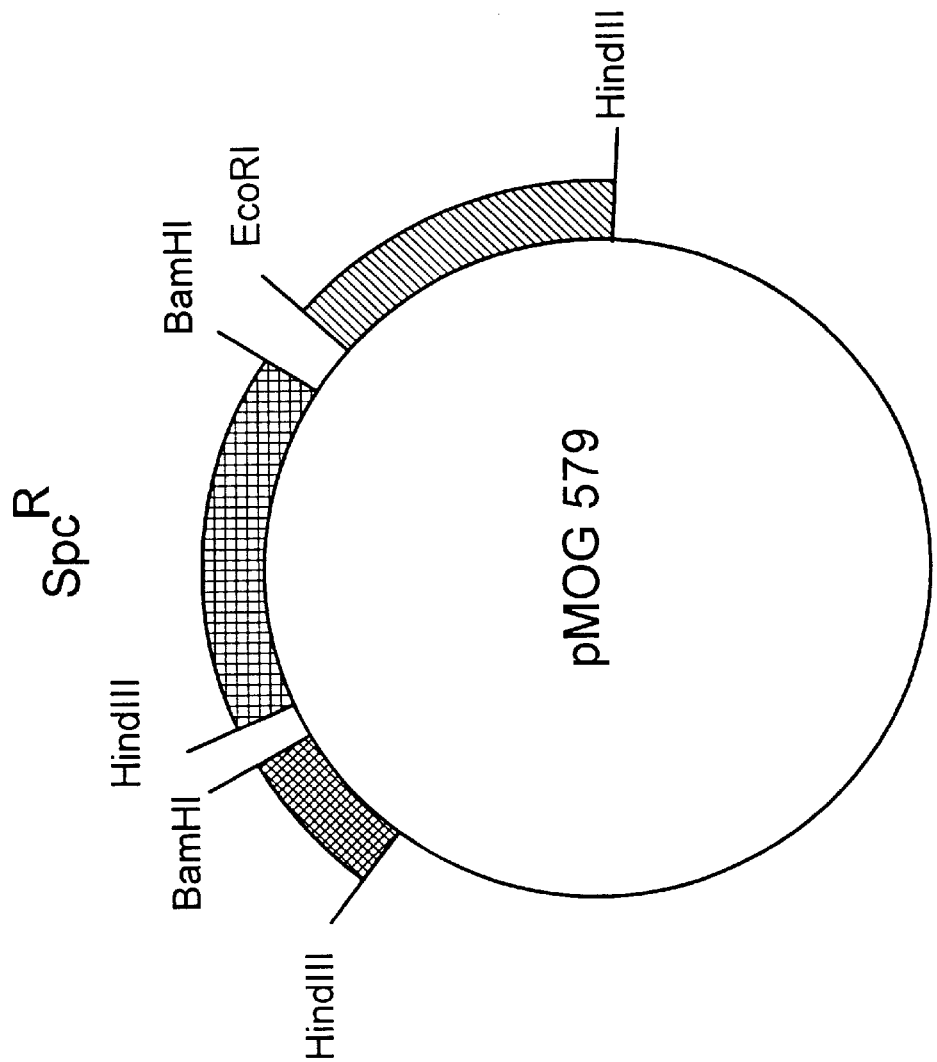
FIG. 6. Schematic representation of pMOG579 used for constructing the helper plasmid without T-region in Agrobacterium strain MOG101.

The Ti-plasmid pTiB6 contains two adjacent T-regions, TL (T-left) and TR (T-right). To obtain a derivative lacking the TL- and TR-regions, we constructed intermediate vector pMOG579. Plasmid pMOG579 is a pBR322 derivative which contains 2 Ti-plasmid fragments homologous to the fragments located left and right outside the T-regions of pTiB6 (shaded in FIGS. 5 and 6). The 2 fragments are separated in pMOG579 by a 2.5 kb BamHI—HindIII fragment from transposon Tn1831 (Hooykaas et al., 1980 Plasmid 4, 64–75) carrying the spectinomycin resistance marker (FIG. 6). The plasmid is introduced into *Agrobacterium tumefanians* strain LBA1010 [C58-C9 (pTiB6)=a cured C58 strain in which pTiB6 is introduced (Koekman at al. (1982), supra), by triparental mating from *E.coli*, using HB101 8pRK2013 as a helper. Transconjugants are selected for resistance to Rifampicin (20 mg/l) and spectinomycin (250 mg/l). A double recombination between pMOG579 and pTiB6 resulted in loss of carbenicillin resistance (the pBR322 marker) and deletion of the entire T-region. Of 5000 spectinomycin resistant transconjugants replica plated onto carbenicillin (100 mg/l) 2 are found sensitive. Southern analysis (not shown) showed that a double crossing over event had deleted the entire T-region. The resulting strain is called MOG101. This strain and its construction is analogous to strain GV2260 (Deblaere et al. 1985, Nucl. Acid Res. 13, 4777–4788).

An alternative helper strain for MOG101 is e.g. LBA4404; this strain can also suitably be used for introduction of a binary plasmid, such as pMOG799 and subsequent plant transformation. Other suitable helper strains are readily available.

Construction of the expression vector pMOG180

The expression vector pMOG180 is a derivative of pMOG18 (EP 0 479 359 A1, Example 2b) wherein the gene coding for GUS is removed and other genes can be inserted between the AlMV RNA4 leader and 3' nos terminator as a BamHI fragment.

Figure 7:
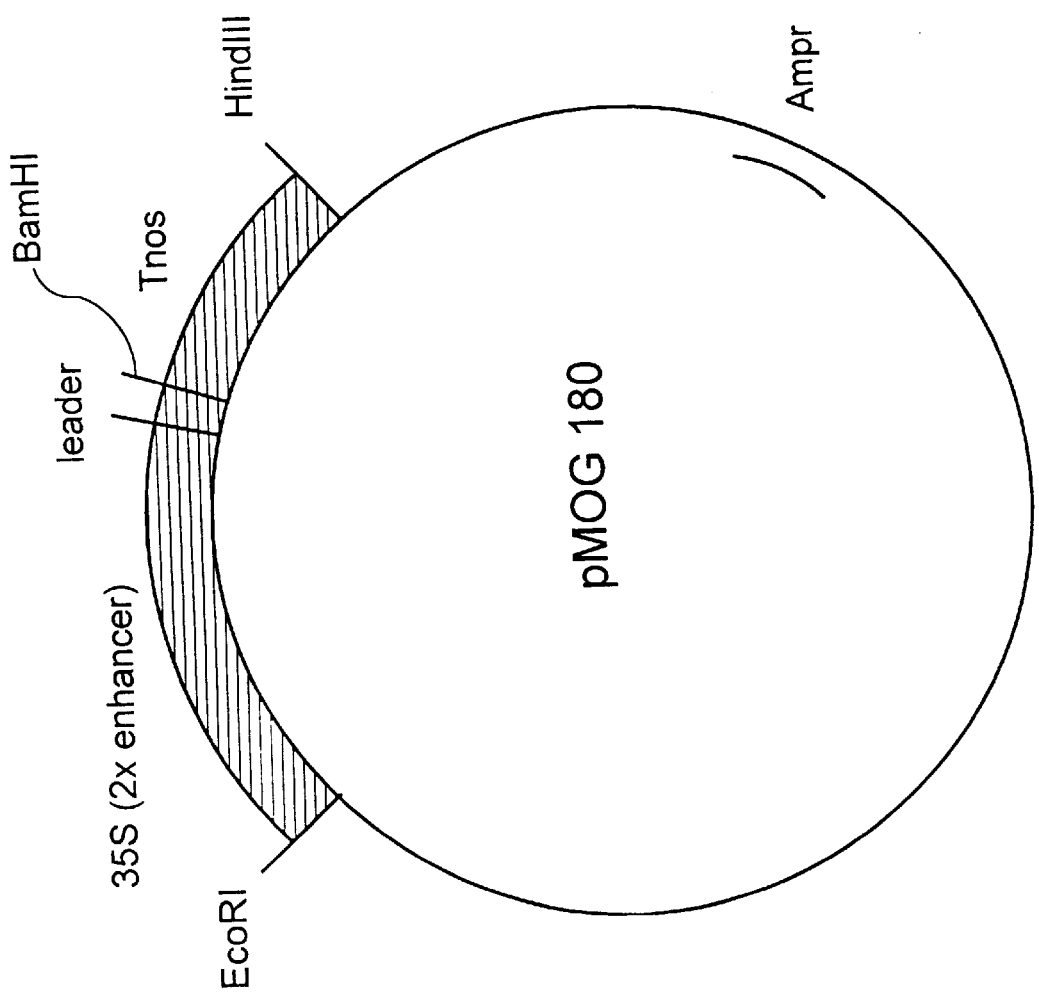
FIG. 7. Schematic representation of expression vector pMOG180.

For this purpose, the EcoRI/NcoI fragment from pMOG18, containing the 35S promoter and ALMV RNA4 leader sequences is synthesized using PCR technology with the primer sets 5' GTTTCTACAGGACGGAGGATCCTG-GAAGTATTTGAAAGA 3' (SEQ ID NO:18) and 5' CAGC-TATGACCATGATTACG 3' (SEQ ID NO:19) thus mutating the NcoI site into a BamHI site. pMOG18 vector is then cut with EcoRI and BamHI after which the newly synthesized EcoRI/BamHI fragment can be ligated between these restriction sites. To circumvent PCR-induced random mutations in the promoter sequences, the EcoRI/EcoRV fragment in the PCR synthesized EcoRI/BamHI fragment is replaced by wildtype sequences from pMOG18. The short EcoRV/BamHI is checked for mutations by sequencing. The resulting expression vector is plasmid pMOG180 (FIG. 7).

Triparental matings

The binary vectors are mobilized in triparental matings with the *E. coli* strain HB101 containing plasmid pRK2013 (Ditta G., Stanfield, S., Corbin, D., and Helinski, D. R. et al. (1980) Proc. Natl. Acad. Sci. USA 77, 7347) into *Agrobacterium tumefaciens* strain MOG101 and used for transformation.

Transformation of tobacco (Nicotiana tabacum SR1)

Tobacco is transformed by cocultivation of plant tissue with Acrobacterium tumefaciens strain MOG101 (Hoekema et al 1983, Nature 303, 179–180) containing the binary vector of interest as described. Transformation is carried out using cocultivation of tobacco (*Ninotiana tabacum* cv. Petit Havana SR1) leaf disks as described by Horsch et al. 1985, Science 227, 1229–1231). Transgenic plants are regenerated from shoots that grow on selection medium containing either kanamycin or hygromycin, depending on the resistance gene present in the binary plasmid, rooted and transferred to soil.

Transformation of potato

Potato (Solanum tuberosum cv. Désiree) is transformed with the Agrobacterium tumefaciens strain MOG101 containing the binary vector of interest as described (Hoekema A., Huisman, M. J., Molendijk, L., Van den Elzen, P. J. M., and Cornelissen, B. J. C. (1989) Bio/technology 7, 273). The basic culture medium is MS30R30, consisting of MS-medium (Murashige, T., and Skoog, F. (1962) Physiol. Plan. 14, 473), supplemented with 30 g/L sucrose, R3 vitamins (Ooms et al. G., Burrell, M. M., Karp, A., Bevan, M., and Hille, J. (1987) Theor. Appl. Genet. 73, 744), 5 $\mu$M zeatin riboside (ZR), and 0.3 $\mu$M indole acetic acid (IAA). The media are solidified where necessary, with 0.7 g/L Daichin agar.

Tubers of Solanum tuberosum cv. Désiree are peeled and surface sterilized for 20 minutes in 0.6% hypochlorite solution containing 0.1% Tween-20. The potatoes are washed thoroughly in large volumes of sterile water for at least 2 hours. Discs of approximately 2 mm thickness are sliced from cylinders of tuber tissue prepared with a corkbore. Discs are incubated for 20 minutes in a suspension consisting of the MS30R3 medium without ZR and IAA, containing $10^6$–$10^7$ bacteria/ml of Agrobacterium MOG101 containing the binary vector. The discs are subsequently blotted dry on sterile filter paper and transferred to solid MS30R3 medium with ZR and IAA. Discs are transferred to fresh medium with 100 mg/L cefotaxim and 50 mg/L vancomycin after 2 days. A week later, the discs are transferred again to the same medium, but this time with 100 mg/L kanamycin to select for transgenic shoots. After 4–8 weeks, shoots emerging from the discs are excised and placed onto rooting medium (MS30R3-medium without ZR and IAA, but with 100 mg/L cefotaxim and 100 mg/L kanamycin). The shoots are propagated axenically by meristem cuttings and transferred to soil after root development. Where appropriate, 10 mg/L hygromycin is used for selection instead of 100 mg/L kanamycin. Transformation of potato cv. Kardal was performed essentially as for cv. Désiree, except for the following modifications: phytohormones in basic culture medium: zeatin riboside 3.5 mg/l; IAA (indole acetic acid) 0.03 mg/l.The Agrobacterium suspension used in the transformation contains $10^5$ to $10^6$ bacteria per milliliter.The concentration of kanamycin in the rooting medium was 50 mg/l.

Trehalose assays

Trehalose is determined essentially as described by Hottiger et al. (Hottiger et al. (1987) J. Bact. 169, 5518). Potato tuber tissue is frozen in liquid nitrogen, powdered with pestle and mortar and subsequently extracted for 60 minutes at room temperature in app. 3 volumes of 500 mM trichloroacetic acid. After centrifugation the pellet is extracted once more in the same way. The combined supernatants from the two extractions are assayed for anthrone positive material (Spiro R. G. (1966) Meth. Enzymol. 8, 3). Trehalose is determined qualitatively by TLC. The extracts are deionized (Merck, Ion exchanger V) and loaded onto Silica Gel 60 plates (Merck). After chromatography plates are developed with n-butanol-pyridine-water (15:3:2, v/v). Spots are visualized by spraying with 5 mg/ml vanillin in concentrated H$_2$SO$_4$ and heating at 130° C. Commercially available trehalose (Sigma) is used as a standard. Alternatively, trehalose was determined quantitatively by anion exchange chromatography with pulsed amperometric detection. Extracts were prepared by adding 1 ml boiling water to 1 g frozen material which was subsequently heated for 15' at 100° C. Samples (25 µl) were analysed on a Dionex DX-300 liquid chromatograph equipped with a 4×250 mm Dionex 35391 carbopac PA-1 column and a 4×50 mm Dionex 43096 carbopac PA-1 precolumn. Elution was with 100 mM NaOH at 1 ml/min. Sugars were detected with a pulsed amperometric detector (Dionex, PAD-2). Commercially available trehalose (Sigma) was used as a standard.

Enzyme assays

In all determinations non-transgenic tuber material or non-transgenic tobacco material was used as a control. Protein content in all samples is determined as described by Bradford (Bradford (1976) Anal. Biochem. 72, 248). For assays on tuber extracts, frozen potato tuber slices of app. 100 mg are homogenized in 100 µl 20 mM HEPES pH 7.4, centrifuged (Eppendorf, 5 minutes at maximum speed). The supernatant is used for activity assays.

SPS activity—SPS activity was determined essentially as described by Amir, J. and Preiss, J. (1982). Plant Physiol. 69, 1027–1030). By changing the composition of the reaction-mixture, two different forms of activity of SPS can be determined; V$_{max}$ and V$_{sel}$. The V$_{max}$ reaction-mixture contained 3.2 mM UDP-glucose, 81 µM [$^{14}$C]-UDP-glucose, 3.2 mM fructose-6-phosphate, 16 mM glucose-6-phosphate, 100 mM Hepes pH 7.4, 20 mM MgCl$_2$ and 5 mM EDTA in a total volume of 50 µl. In the V$_{sel}$ reaction-mixture, the concentration of fructose-6-phosphate and glucose-6-phospate is halved and 5 mM inorganic phosphate is added. As a control, SPS activity is measured in the V$_{max}$ reaction mixture without fructose-6-phosphate and glucose-6-phosphate. The reaction is carried out at room temperature for 30' and stopped by heating the mixture for 5' at 95° C. The products of the reaction are treated with alkaline phophatase and the resulting [$^{14}$C]-sucrose is separated from the substrates by ion exchange chromatography. The amount of radiolabeled sucrose formed in the reaction is measured in a scintillation-counter.

TPS activity—TPS activity was measured in a similar way as described for SPS. After ion exchange chromatography the samples contained dephosphorylated sucrose as well as trehalose. To determine which proportion of the formed products is trehalose, samples were separated by TLC as described. The extracts were deionized (Merck, Ion exchanger V) and loaded onto Silica Gel 60 plates (Merck). After chromatography, spots containing [$^{14}$C]-sucrose and [$^{14}$C]-trehalose were scraped off and measured in a scintillation-counter.

AGPase activity—AGPase activity is determined as described by Müller-Röber et al. (Müller-Röbber B., Sonnewald, U., and Willmitzer, L. (1992) EMBO J. 11, 1229). Production of glucose-1-phosphate from ADP-glucose is determined in a NAD-linked glucose-6-phosphate dehydrogenase system. The reaction assay contained 80 mM HEPES pH 7.4, 10 mM MgCl$_2$, 1 mM ADP-glucose, 0.6 mM NAD, 10 µM glucose-1,6-diphosphate, 3 mM DTT, 0.02% bovine serum albumin, 1 U phosphoglucomutase from rabbit muscle (Sigma), 2.5 U NAD-linked glucose-6-phosphate dehydrogenase from *Leuconostoc mesenteronides* and tuber extract. The reaction is initiated by addition of sodiumpyrophosphate to a final concentration of 2 mM. NAD reduction is measured spectrophotometrically at 340 nm and 30° C. A unit of AGPase activity is defined as nmol glucose-1-phosphate generated per min at 30° C.

EXAMPLE I

Cloning of a full length *E. coli* otsA gene

In *E.coli* trehalose phosphate synthase (TPS) is encoded by the otsA gene located in the operon otsBA. The location and the direction of transcription of this operon on the *E.coli* chromosome are known (Kaasen, I., Falkenberg, P., Styrvold, O. B., and Ström, A. R. (1992) J. Bact. 174, 889). The OtSA gene is located at 42', and according to Kaasen et al. confined on a 18.8 kb fragment present in the EMBL4 genomic clone designated 7F11 of the map by Kohara et al. (Kohara, Y., Akiyama, K., and Isono, K. (1987) Cell 50, 495). DNA prepared from a lysate of lambda clone 7F11, and digested with HindIII. The isolated 2.9 kb HindIII fragment (the 'right-hand' HindIII site at 14.3 kb in the insert was omitted on the map by Kohara et al., as already noticed by Kaasen et al.) is cloned in pUC18 linearized with HindIII. The 2.9 kb HindIll insert from the resulting plasmid, designated pMOG674, is sequenced. The sequence is found to contain part of the LAH gene of the arabinose transport operon (Scripture, J. B., Voelker, C., Miller, S., O'Donnell, R. T., Polgar, L., Rade, J., Horazdovsky, B. F., and Hogg, R. W. (1987) J. Mol. Biol. 197, 37), the otsB gene encoding TPP as localized by Kaasen et al. and part of the otaA gene encoding TPS. The otsA is found not to be confined to the 2.9 kb HindIII fragment as described by Kaasen et al. To complete the sequence an overlapping BamHI/EcoRI fragment is isolated and partially sequenced. The complete TPS-encoding sequence of the otsA gene is shown in SEQ ID NO: 2. The position of the otsA gene on clone 7F11, with the restriction enzyme sites used, is shown in FIG. 8. An additional HindIII site not present on the map published by Kohara et al. is found on the 'left-hand' site of the 2.9 kb HindIII fragment. The HindIII site in pMOG180 is replaced by a SstI site, by cloning the oligonucleotide duplex:

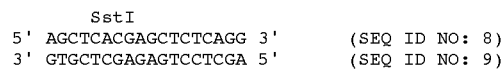

```
        SstI
5' AGCTCACGAGCTCTCAGG 3'         (SEQ ID NO: 8)
3' GTGCTCGAGAGTCCTCGA 5'         (SEQ ID NO: 9)
``` into pMOG180 cut with HindIII. The resulting vector is designated pMOG746. The oligonucleotide duplex:

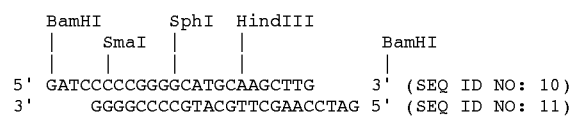

```
   BamHI      SphI   HindIII
   |   SmaI   |      |              BamHI
   |   |      |      |              |
5' GATCCCCCGGGGCATGCAAGCTTG    3'  (SEQ ID NO: 10)
3'     GGGGCCCCGTACGTTCGAACCTAG 5' (SEQ ID NO: 11)
``` is cloned in vector pMOG746 linearized with BamHI. The vector with the oligonucleotide duplex in the desired orientation (checked by restriction enzyme digestion) is designated pMOG747. The 2.9 kb HindIII fragment of plasmid pMOG674 is cloned in pMOG747 linearized with HindIII, resulting in vector pMOG748. The app. 2.4 kb EcoRV/SstI and the app. 3.5 kb SstI/SmaI fragments of pMOG748 are isolated, ligated and transformed into *E. coli*, thus deleting the 3' end of the 2.9 kb HindIII fragment. The resulting plasmid is designated pMOG749. The 5' end of the otsA gene is synthesized by PCR using the synthetic oligonucleotides TPS1 and TPS2 with pMOG749 as a template.

```
TPS1    5' GAGAAAATACCCGGGGTGATGAC 3'      (SEQ ID NO: 12)
TPS2    5' GATAATCGTGGATCCAGATAATGTC 3'    (SEQ ID NO: 13)
```

By sequencing it is confirmed that the 0.4 kb PCR fragment has the correct sequence. The 1 kb BamHI/HindIII fragment of pMOG749 is cloned together with the 0.4 kb XmaI/BamHI PCR fragment in pMOG747 linearized with XmaI and HindIII. In the resulting plasmid, digested with HindIII and SstI, the synthetic oligonucleotide duplex TPS6/7 is cloned, encoding the three C-terminal amino acids of TPS.

```
            LysLeuAlaStop
TPS 6/7: 5' AGCTGGCGTGAGGAGCGGTTAATAAGCTTGAGCT 3'  (SEQ ID NO: 20)
         3'     CCGCACTCCTCGCCAATTATTCGAAC     5'  (SEQ ID NO: 21)
```

Figure 9:
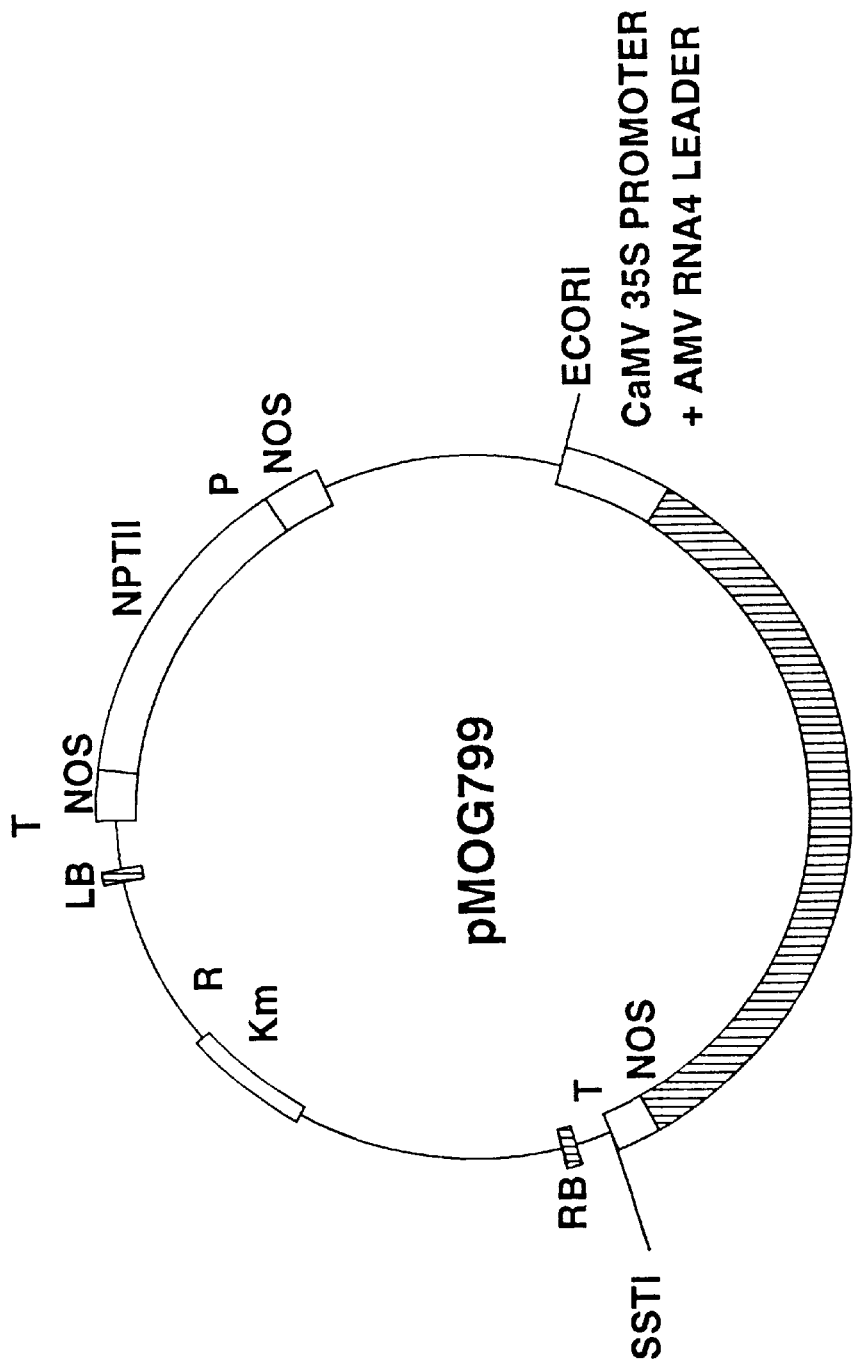
FIG. 9. Schematic representation of binary vector pMOG799.

In the resulting plasmid, digested with HindIII and SstI, the 0.25 kb HindIII/SstI fragment of plasmid pMOG749 is cloned, comprising the terminator from the *Agrobacterium tumefaciens* nopaline synthase (NOS) gene, resulting in plasmid pMOG798. This plasmid contains the *E. coli* otsA gene in the correct orientation under control of the Cauliflower Mosaic virus (CaMV) 35S promoter with double enhancer (Guilley et al. (1982) Cell 30, 763), the Alfalfa Mosaic Virus (AMV) RNA4 leader sequence (Brederode et al. (1980) Nucl. Acids Res. 8, 2213) and the nopaline synthase transcription terminator sequence from *Agrobacterium tumefaciens*. The entire expression cassette is cloned as a 2.5 kb EcoRI/SstI fragment into the binary vector pMOG23 linearized with EcoRI and SstI. The resulting binary vector, pMOG799 (FIG. 9), is used to transform potato and tobacco (An *E. coli* strain harboring pMOG799 has been deposited at the Centraal Bureau voor Schimmelcultures, Phabagen collections, Padualaan 8, Utrecht, The Netherlands, on Aug. 23, 1993, deposit number CBS 430.93; pMOG23 has been deposited at the CBS on Jun. 9, 1990, deposit number CBS 102.90).

EXAMPLE II

Trehalose production in tobacco trans formed with pMOG799

Tobacco leaf discs are transformed with the binary vector pMOG799 using *Agrobacterium tumefaciens*. A number of 20 independent transgenic shoots are analysed for trehalose phosphate synthase (TPS) activity. Some tobacco plants grown in vitro were found to have extremely thick roots compared to untransformed plants. Analysis of the roots of those transgenic tobacco plants show elevated levels of trehalose in comparison with non-transgenic control plants.

EXAMPLE III

Trehalose production in potatoes transformed with pMOG799

Potato tuber discs are transformed with the binary vector pMOG799 using *Agrobacterium tumefaciens*. Transgenic shoots are selected on kanamycin. A number of 20 independent transgenic shoots are analyzed for trehalose phosphate synthase (TPS) activity. Shoots found to contain the enzyme are grown to mature plants. Analyses of mature tubers of those transgenic potato plants show elevated levels of trehalose in comparison with non-transgenic control plants. Transgenic plant line MOG799.1 is propagated for further work.

EXAMPLE IV

Construction of pMOG664

Two oligonucleotides corresponding to the cDNA sequence of the small subunit of ADP-glucose pyrophosphorylase (AGPaseB) from potato tuber cv. Désiree (Müller-Röber, B., Kossmann, J., Hannah, L. C., Willmitzer, L., and Sonnewald, U. (1990) Mol. Gen. Genet. 224, 136–146) are synthesized:

```
5' TCCCCATGGAATCAAAGCATCC 3'   (SEQ ID NO: 4)
5' GATTGGATCCAGGGCACGGCTG 3'   (SEQ ID NO: 5)
```

Figure 4:
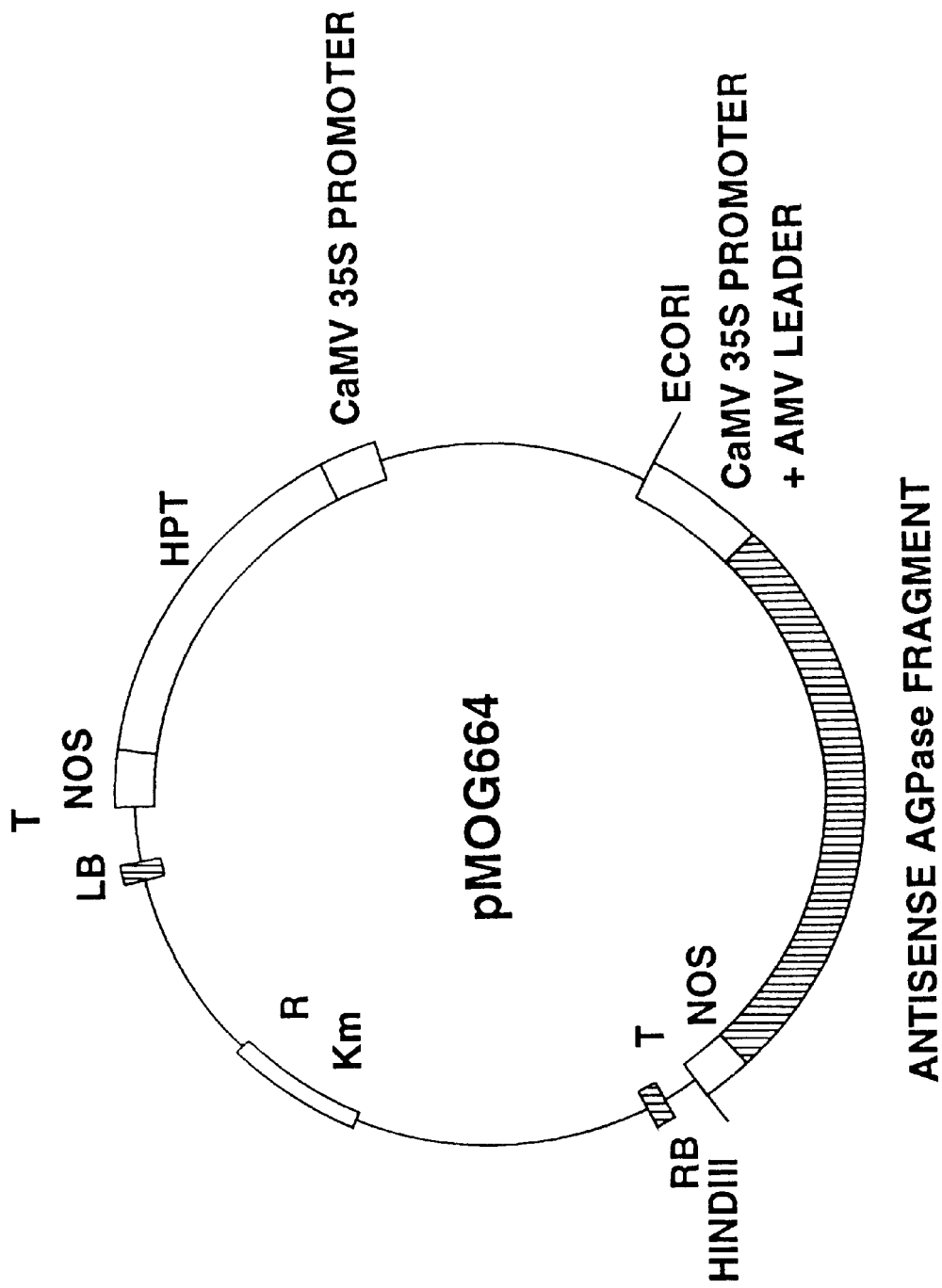
FIG. 4. Schematic representation of binary vector pMOG664.

The oligonucleotides are designed to contain suitable restriction sites (BamHI and NcoI, underlined) at their termini to allow assembly in an expression cassette in an antisense orientation after digestion with these enzymes. A fragment of about 1 kb is PCR amplified with these oligonucleotides using DNA isolated from a cDNA library from potato cv. Désiree prepared from 2 month old leaf tissue (Clontech) as a template. By sequencing it is shown, that the fragment is identical with the AGPase B sequence from potato cv. Désiree (Müller-Röber, B., Kossmann, J., Hannah, L. C., Willmitzer, L., and Sonnewald, U. (1990) Mol. Gen. Genet. 224, 136–146). Following digestion with BamHI and NcoI, the fragment is cloned in pMOG18 linearized with BamHI and NcoI. From the resulting plasmid the 1.85 kb EcoRI/BamHI fragment (containing the CaMV 35S promoter, the AMV RNA4 leader and the AGPase fragment in an antisense orientation), as well as the BamHI/HindIII fragment containing the terminator from the nopaline synthase (NOS) gene from *Agrobacterium tumefaciens* are cloned in a three-way ligation in the binary vector pMOG22 linearized with EcoRI and HindIII. The binary vector pMOG22 contains a plant expressible HPTII gene for hygromycin selection in transgenic plants (pMOG22 has been deposited at the Centraal Bureau voor Schimmelcultures on Jan. 29, 1990 under accession number 101.90). The resulting binary vector pMOG664 (FIG. 4) is used for potato transformation.

EXAMPLE V

Construction of pMOG801

A set of oligonucleotides complementary to the sequence of the maize sucrose phosphate synthase (SPS) cDNA (Worrell, A. C., Bruneau, J-M., Summerfalt, K., Boersig, M., and Voelker, T. A. (1991) Plant Cell 3, 1121) is synthesized. Their sequences are as follows:

```
5' CTAGGTCGTGATTCTGATACAGGTGGCCAGGTG    3'   (SEQ ID NO: 6)
5' CAGCATCGGCATAGTGCCCATGTATCACGTAAGGC  3'   (SEQ ID NO: 7)
```

These oligonucleotides are used to PCR amplify a DNA fragment of 370 bp using DNA isolated from a potato cv. Désiree cDNA library prepared from 2 months old leaf tissue (Clontech) as a template. By sequencing of this fragment it is shown, that it is homologous to the SPS sequence of maize (see FIG. 3, and Worrell et al. (1991). The PCR fragment is used to screen a lambda gt10 library of potato cv. Désiree cDNA library prepared from 2 month old leaf tissue (Clontech). The insert of one positively hybridizing clone is sequenced. The sequence of the 654 bp DNA fragment is found to be 65% identical with the corresponding part of the maize SPS sequence (Starting at nucleotide number 349 in FIG. 11 in Worrell et al. (1991). The EcoRI insert of this clone is cloned in pMOG180 digested with BamHI, in a three-way ligation with the following synthetic oligonuclotide duplex.

```
5' GATCGTCAGATCTAGC 3'    (SEQ ID NO: 14)
3' CAGTCTAGATCGTTAA 5'    (SEQ ID NO: 15)
```

Figure 10:
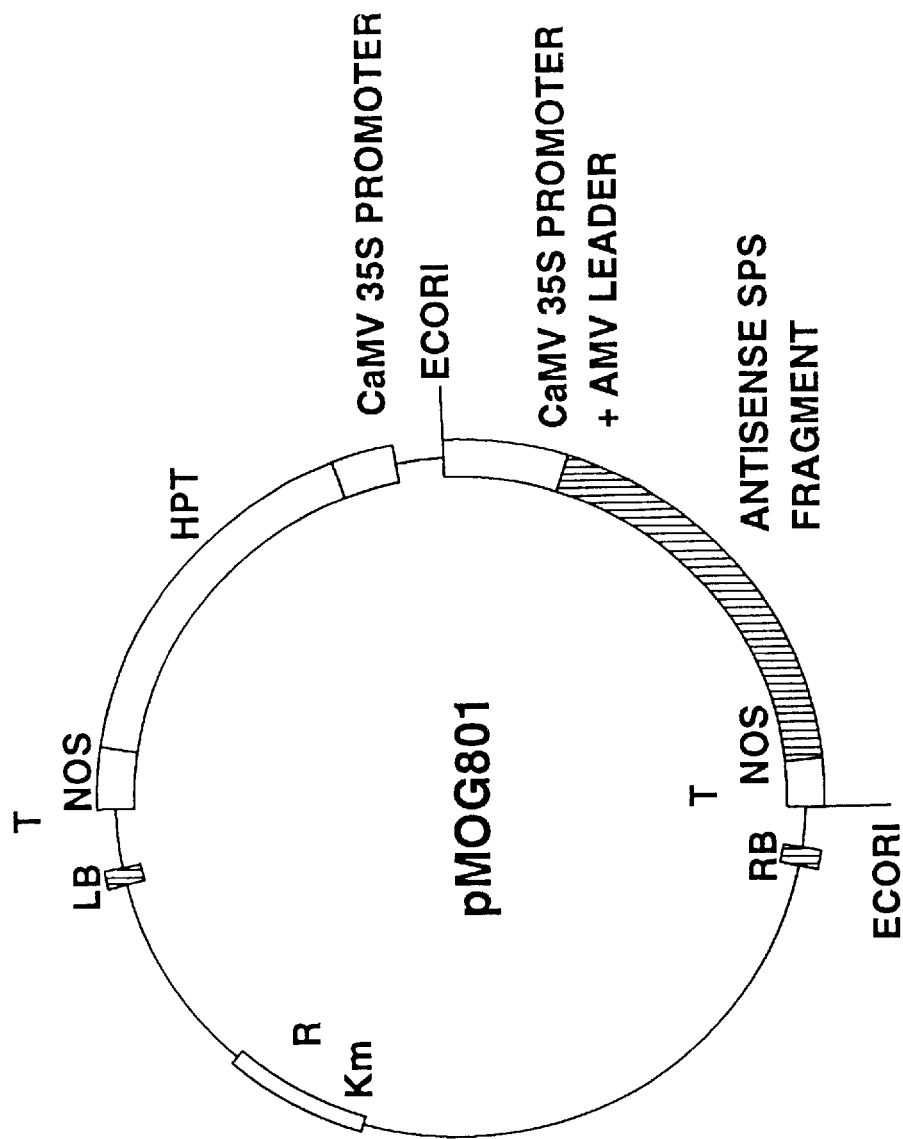
FIG. 10. Schematic representation of binary vector pMOG801.

The plasmid, having the SPS fragment in the antisense orientation with respect to the CaMV 35S promoter, is designated pMOG787. The EcoRI/HindIII fragment of plasmid pMOG787 is cloned in a three-way ligation with a synthetic linker:

```
5' AGCTTCCCCCCCG 3'    (SEQ ID NO: 16)
3' AGGGGGGGCTTAA 5'    (SEQ ID NO: 17)
``` into the binary vector pMOG22 linearized with EcoRI. The binary vector pMOG22 contains a plant expressible HPTII gene for hygromycin selection in transgenic plants (pMOG22 has been deposited at the Centraal Bureau voor Schimmelcultures on Jan. 29, 1990 under accession number 101.90). The resulting binary vector pMOG801 (FIG. 10) is used for potato transformation.

EXAMPLE VI

Construction of pMOG802

Figure 11:
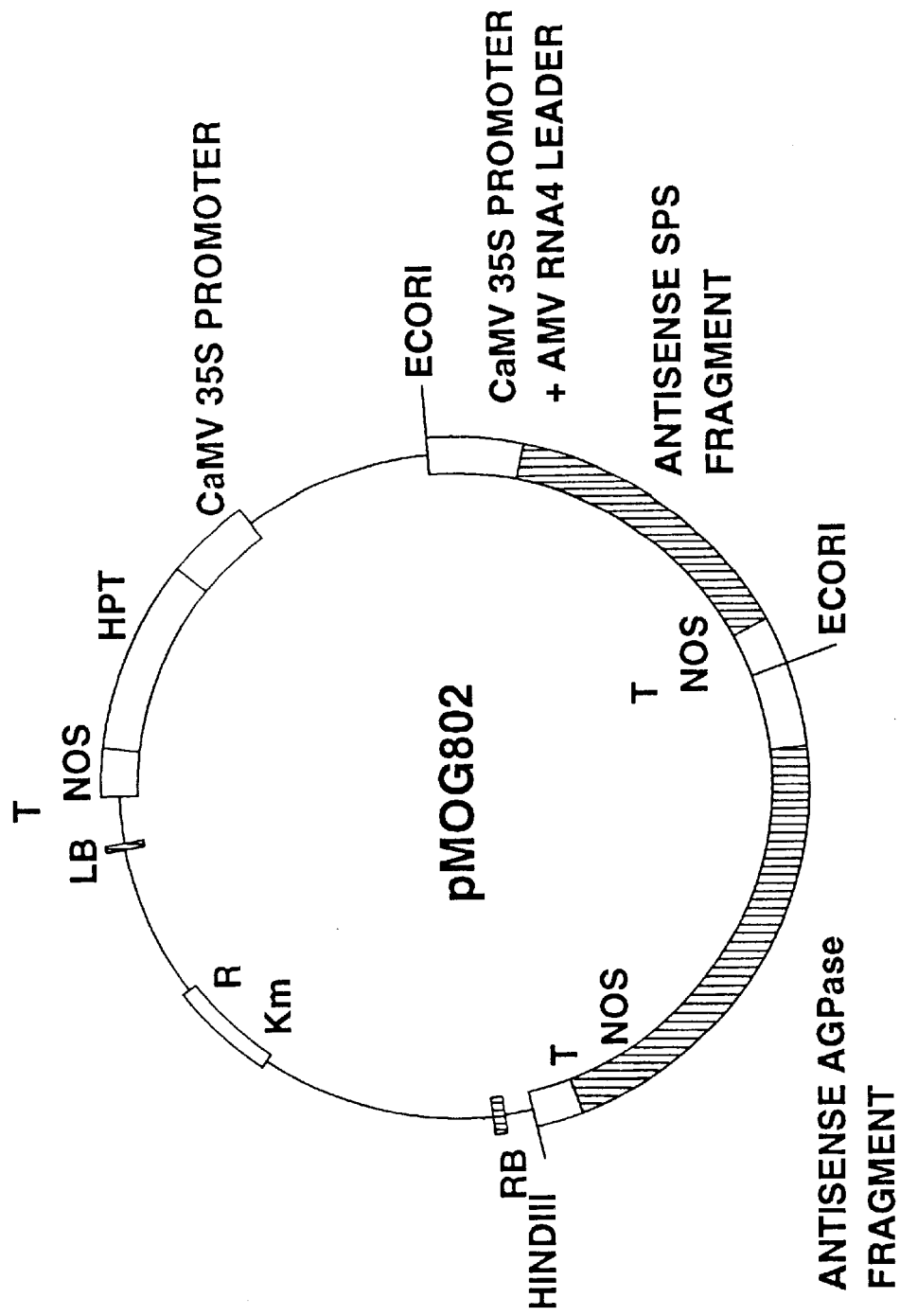
FIG. 11. Schematic representation of binary vector pMOG802.

The EcoRI fragment of plasmid pMOG801, containing the antisense SPS expression cassette, is cloned in the binary vector pMOG664 (containing the antisense AGPase cassette), linearized with EcoRI. The resulting binary vector is called pMOG802 (FIG. 11).

EXAMPLE VII

Trehalose production in potato transformed with pMOG799 and pMOG664

Potato tuber discs of kanamycin resistant plant line MOG799.1, expressing TPS (Example IX) are transformed with the binary vector pMOG664, containing the antisense AGPase expression cassette. Transgenic shoots, selected on 10 mg/L hygromycin, are analyzed for the presence of the TPS and antisense AGPase sequences by PCR. Transgenic plants containing both are analyzed for TPS and AGPase activity.

By analysis of transgenic tubers for AGPase activity it is shown that, reductions in activity levels in individual transgenic lines in comparison with non-transgenic controls occur. By Northern blots it is shown, that mRNA levels for AGPase are reduced in the transgenic plants compared to those in non-transgenic control plants. Trehalose levels in tubers of transgenic potato plants, found to exhibit TPS activity, and having reduced levels of AGPase, show an increase in comparison with the levels found in tubers of transgenic plant line MOG799.1.

EXAMPLE VIII

Trehalose production in potato transformed with pMOG799 and pMOG801

Potato tuber discs of kanamycin resistant plant line MOG799.1, expressing TPS (Example IX) are transformed with the binary vector pMOG801, containing the antisense SPS expression cassette. Transgenic shoots, selected on 10 mg/L hygromycin, are analyzed for the presence of the TPS and antisense SPS sequences by PCR. Transgenic plants containing both are analyzed for TPS and SPS activity.

By analysis of transgenic tubers for SPS activity it is shown that reductions in activity levels in individual transgenic lines in comparison with non-transgenic controls occur. By Northern blots it is shown, that mRNA levels for SPS are reduced in the transgenic plants compared to those in non-transgenic control plants. Trehalose levels in tubers of transgenic potato plants, found to exhibit TPS activity, and having reduced levels of SPS, show an increase in comparison with the levels found in tubers of transgenic plant line MOG799.1.

EXAMPLE IX

Trehalose production in potato transformed with pMG799 and pMOG802

Potato tuber discs of kanamycin resistant plant line MOG799.1, expressing TPS (Example IX) are transformed with the binary vector pMOG802, containing the antisense SPS and AGPase expression cassettes. Transgenic shoots, selected on 10 mg/L hygromycin, are analyzed for the presence of the TPS, antisense AGPase and antisense SPS sequences by PCR. Transgenic plants containing all three constructs are analyzed for TPS, AGPase and SPS activity.

By analysis of transgenic tubers for AGPase and SPS activity it is shown, that reductions in the activity levels for both enzymes in individual transgenic lines in comparison with non-transgenic controls occur. By Northern blots it is shown that mRNA levels for AGPase and SPS are reduced in the transgenic plants compared to those in non-transgenic control plants. Trehalose levels in tubers of transgenic potato plants, found to exhibit TPS activity, and having reduced levels of SPS, show an increase in comparison with the levels found in tubers of transgenic plant line MOG799.1.

Deposited strains pMOG22; Deposit No. CBS 101.90 (page 23, lines 18–21; page 24, lines 21–23) pMOG23; Deposit No. CBS 102.90 (page 22, line 10) pMOG799; Deposit No. CBS 430.93 (page 22, line 6)

We claim:

1. An isolated DNA molecule comprising a plant expressible promoter operatively coupled to a coding sequence encoding an *E. coli* full length trehalose phosphate synthase.

2. The isolated DNA molecule according to claim 1, which codes for the amino acid sequence of SEQ ID NO:3.

3. The isolated DNA molecule according to claim 1 comprising the DNA sequence of SEQ ID NO:2.

4. A nucleic acid comprising (i) a DNA molecule which, when expressed in a plant or plant cell, increases the trehalose content of said plant or plant cell, said DNA molecule encoding a trehalose phosphate synthase having the amino acid sequence shown in SEQ ID NO:3, and (ii) a plant expressible promoter operatively coupled to said DNA molecule.

5. A nucleic acid which comprises in operable linkage:
   a) a transcriptional initiation region that is functional in a plant or plant cell, and
   b) a DNA molecule encoding an *E. coli* trehalose phosphate synthase.

6. The nucleic acid as claimed in claim 5 wherein the DNA molecule comprises the DNA sequence of the open reading frame of the otsA gene of *E. coli*.

7. The nucleic acid according to claim 5 further comprising a transcriptional termination sequence that is functional in said plant or plant cell.

8. A nucleic acid which comprises in operable linkage:
   a) a transcriptional initiation region that is functional in a plant or plant cell; and
   b) a DNA molecule encoding a trehalose phosphate synthase, said trehalose phosphate synthase having the amino acid sequence shown in SEQ ID NO:3.

9. The nucleic acid according to claim 8, further comprising a transcription terminator region that is functional in said plant or plant cell.

10. A nucleic acid according to claim 9, wherein said transcriptional initiation region comprises a promoter region of the 35S RNA encoding DNA of the cauliflower mosaic virus and wherein the transcription terminator region is that of the nopaline synthase gene of *Agrobacterium tumefaciens*.

11. The nucleic acid as claimed in claim 10, wherein said nucleic acid is in pMOG799.

12. A cloning vector which comprises a nucleic acid according to claim 4.

13. microorganism comprising a vector according to claim 12, said microorganism being of the genus Agrobacterium.

14. A method for obtaining a plant with increased trehalose production comprising the steps of:
   1) introducing into a recipient cell of a plant, a plant expressible gene which when expressed in a plant or plant cell increases the trehalose content of said plant or plant cell, said plant expressible gene being an *E. coli* trehalose phosphate synthase gene and said plant expressible gene being operably linked to:
      a) a transcriptional initiation region that is functional in said plant, and
      b) a DNA molecule encoding a selectable marker gene that is functional in said plant, and
   2) regenerating a plant from the recipient cell under conditions that allow for selection for the presence of the selectable marker gene.

15. The method according to claim 14, wherein the plant expressible gene encodes a full length trehalose phosphate synthase found naturally in *E. coli*.

16. The method according to claim 14, wherein the plant expressible gene further comprises a transcriptional termination sequence that is functional in said plant.

17. A recombinant plant genome which comprises a nucleic acid encoding an *E. coli* trehalose phosphate synthase.

18. A plant cell comprising the recombinant plant genome of claim 17.

19. A plant cell culture comprising the plant cell of claim 18.

20. A plant comprising the plant cell of claim 18.

21. A plant that produces increased levels of trehalose as a result of genetic modification with a nucleic acid encoding an *E. coli* trehalose phosphate synthase.

22. The plant according to claim 21, which is not *Arabidopsis thaliana*.

23. The plant of claim 21, said plant belonging to the Angiospermae.

24. The plant according to claim 21 which is from the family Solanaceae.

25. The plant according to claim 21 which is *Solanum tuberosum*.

26. A plant part of the plant according to claim 21.

27. The plant part according to claim 26 selected from the group consisting of bulbs, flowers, fruits, hairy roots, leaves, microtubers, pollen, roots, seeds, stalks and tubers.

28. A method of preserving a plant or plant part in the presence of trehalose, comprising the steps of:
   1) growing a plant of any one of claims 21–23 or a plant part of claim 26 or
   2) harvesting the plant or the plant part which comprises trehalose, and
   3) air drying or freeze drying the plant or plant part.

29. A dried plant or plant part which is obtained by the method of claim 28.

30. A method for the production of trehalose comprising the steps of:
   1) growing the plant of claim 21 to allow production of trehalose,
   2) harvesting said plant or a part thereof,
   3) isolating trehalose from said plant or said part thereof.

* * * * *